(12) United States Patent
Guy et al.

(10) Patent No.: US 7,285,569 B2
(45) Date of Patent: Oct. 23, 2007

(54) TRICYCLES, THEIR MANUFACTURE AND USE AS PHARMACEUTICAL AGENTS

(75) Inventors: Georges Guy, Habach (DE); Bernhard Goller, Penzberg (DE); Hans-Willi Krell, Penzberg (DE); Klaus-Peter Kuenkele, Benediktbeuern (DE); Anja Limberg, Penzberg (DE); Petra Rueger, Penzberg (DE); Matthias Rueth, Penzberg (DE)

(73) Assignee: Hoff Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/233,408

(22) Filed: Sep. 23, 2005

(65) Prior Publication Data

US 2006/0069145 A1    Mar. 30, 2006

(30) Foreign Application Priority Data

| Sep. 24, 2004 | (EP) | ................................. | 04022753 |
| Dec. 17, 2004 | (EP) | ................................. | 04030113 |
| May 13, 2005 | (EP) | ................................. | 05010528 |

(51) Int. Cl.
*A61K 31/4184* (2006.01)
*A61K 31/4155* (2006.01)
*C07D 487/02* (2006.01)
*C07D 403/04* (2006.01)

(52) U.S. Cl. ...................... 514/394; 514/395; 514/406; 548/302.1; 548/366.1; 548/365.1

(58) Field of Classification Search ............. 548/302.1, 548/364.7, 365.1, 366.1; 514/394, 395, 406
See application file for complete search history.

(56) References Cited

U.S. PATENT DOCUMENTS

| 4,695,567 | A | 9/1987 | Mertens et al. |
| 4,835,280 | A | 5/1989 | Martens et al. |
| 4,863,945 | A | 9/1989 | Friebe et al. |
| 4,954,498 | A | 9/1990 | Mertens et al. |
| 4,981,864 | A | 1/1991 | Von der Saal et al. |
| 5,116,843 | A | 5/1992 | Mertens et al. |
| 5,212,186 | A | 5/1993 | Paal et al. |
| 6,207,401 | B1 | 3/2001 | Plowman et al. |

FOREIGN PATENT DOCUMENTS

| DE | 34 17 643 | 11/1985 |
| DE | 36 42 315 | 6/1988 |
| DE | 37 01 277 | 7/1988 |
| EP | 0 189 103 | 7/1986 |
| EP | 0 318 902 | 6/1989 |
| EP | 1 051 500 | 11/2000 |
| WO | WO95/19169 | 7/1995 |
| WO | WO95/23141 | 8/1995 |
| WO | WO97/22702 | 6/1997 |
| WO | WO97/42187 | 11/1997 |
| WO | WO99/06396 | 2/1999 |
| WO | WO 00/44728 | 8/2000 |
| WO | WO 00/47212 | 8/2000 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/55116 | 8/2001 |
| WO | WO 01/77085 | 10/2001 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/057259 | 7/2002 |
| WO | WO 02/059111 | 8/2002 |
| WO | WO 02/059112 | 8/2002 |
| WO | WO 02/062789 | 8/2002 |

(Continued)

OTHER PUBLICATIONS

Hunter, T., Cell 50 (1987) 823-829.

(Continued)

*Primary Examiner*—Rebecca Anderson
*Assistant Examiner*—Yong Chu
(74) *Attorney, Agent, or Firm*—George W. Johnston; Patricia S. Rocha-Tramaloni

(57) ABSTRACT

The present invention relates to compounds of formula I

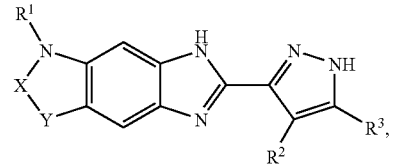

formula I their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

11 Claims, No Drawings

FOREIGN PATENT DOCUMENTS

| WO | WO 02/066461 | 8/2002 |
| --- | --- | --- |
| WO | WO 02/068415 | 9/2002 |
| WO | WO 02/96905 | 12/2002 |
| WO | WO 03/035065 | 5/2003 |
| WO | WO 03/077921 | 9/2003 |
| WO | WO 03/078423 | 9/2003 |
| WO | WO 03/078426 | 9/2003 |
| WO | WO 03/078427 | 9/2003 |
| WO | WO 04/000833 | 12/2003 |
| WO | WO 04/005283 | 1/2004 |
| WO | WO 2004/063151 | 7/2004 |

OTHER PUBLICATIONS

Bischoff, J.R., and Plowman, G.D., Trends Cell Biol. 9 (1999) 454-459.

Giet, R., and Prigent, C., J. Cell Sci. 112 (1999) 3591-3601.

Nigg, E.A., Nat. Rev. Mol. Cell Biol. 2 (2001) 21-32.

Adams, R.R., et al., Trends Cell Biol. 11 (2001) 49-54.

Sen, S., et al., J. Natl.Cancer Inst. 94 (2002) 1320-1329.

Isola, J.J., et al., Am. J. Pathology 147 (1995) 905-911.

Harrington, E.A., et al., Nat. Med. 10 (2004) 262-267.

Mertens, A. et. al. J. Med. Chem. 30 (1987) 1279-1287.

Von der Saal, W., et. al., J. Med. Chem 32 (1989) 1481-1491.

Mahadevan, et. al., Curr. Med. Chem-Anti cancer Agents (2003) 3, 25-34.

Konno, Yasuo, et al., Chemical Abstracts, XP002317149 (2004).

Dang, T.D., et al., Polymer Preprints (American Chemical Society, Division of Polymer Chemistry), 41(1), 217-218, (2000), XP008042595.

TRICYCLES, THEIR MANUFACTURE AND USE AS PHARMACEUTICAL AGENTS

PRIORITY TO RELATED APPLICATIONS

This application claims the benefit of European Application Nos. 04022753.0, filed Sep. 24, 2004, No. 04030113.7, filed Dec. 17, 2004, and No. 05010528.7, filed May 13, 2005.

BACKGROUND OF THE INVENTION

The present invention relates to novel tricycles, to a process for their manufacture, pharmaceutical compositions containing them and their manufacture as well as the use of these compounds as pharmaceutically active agents.

Protein kinases regulate many different signaling processes by adding phosphate groups to proteins (Hunter, T., Cell 50 (1987) 823-829); particularly serine/threonine kinases phosphorylate proteins on the alcohol moiety of serine or threonine residues. The serine/threonine kinase family includes members that control cell growth, migration, differentiation, gene expression, muscle contraction, glucose metabolism, cellular protein synthesis, and regulation of the cell cycle.

The Aurora kinases are a family of serine/threonine kinases that are believed to play a key role in the protein phosphorylation events that are essential for the completion of essential mitotic events. The Aurora kinase family is made up of three key members: Aurora A, B and C (also known as Aurora-2, Aurora-1 and Aurora-3 respectively). Aurora-1 and Aurora-2 are described in U.S. Pat. No. 6,207,401 of Sugen and in related patents and patent applications, e.g. EP 0 868 519 and EP 1 051 500.

For Aurora A there is increasing evidence that it is a novel proto-oncogene. Aurora A gene is amplified and transcript/protein is highly expressed in a majority of human tumor cell lines and primary colorectal, breast and other tumors. It has been shown that Aurora A overexpression leads to genetic instability shown by amplified centrosomes and significant increase in aneuploidy and transforms Rat1 fibroblasts and mouse NIH3T3 cells in vitro. Aurora A-transformed NIH3T3 cells grow as tumors in nude mice (Bischoff, J. R., and Plowman, G. D., Trends Cell Biol. 9 (1999) 454-459; Giet, R., and Prigent, C., J. Cell Sci. 112 (1999) 3591-3601; Nigg, E. A., Nat. Rev. Mol. Cell Biol. 2 (2001) 21-32; Adams, R. R., et al., Trends Cell Biol. 11 (2001) 49-54). Moreover, amplification of Aurora A is associated with aneuploidy and aggressive clinical behavior (Sen, S., et al., J. Natl. Cancer Inst. 94 (2002) 1320-1329) and amplification of its locus correlates with poor prognosis for patients with node-negative breast cancer (Isola, J. J., et al., Am. J. Pathology 147 (1995) 905-911). For these reasons it is proposed that Aurora A overexpression contributes to cancer phenotype by being involved in chromosome segregation and mitotic checkpoint control.

Human tumor cell lines depleted of Aurora A transcripts arrest in mitosis. Accordingly, the specific inhibition of Aurora kinase by selective inhibitors is recognized to stop uncontrolled proliferation, re-establish mitotic checkpoint control and lead to apoptosis of tumor cells. In a xenograft model, an Aurora inhibitor therefore slows tumor growth and induces regression (Harrington, E. A., et al., Nat. Med. 10 (2004) 262-267).

Low molecular weight inhibitors for protein kinases are widely known in the state of the art. For Aurora inhibition such inhibitors are based on i.e. quinazoline derivatives as claimed in the following patents and patent applications: WO 00/44728; WO 00/47212; WO 01/21594; WO 01/21595; WO 01/21596; WO 01/21597; WO 01/77085; WO 01/55116; WO 95/19169; WO 95/23141; WO 97/42187; WO 99/06396; pyrazole and triazole derivatives as claimed in the following patents and patent applications: WO 02/22601; WO 02/22602; WO 02/22603; WO 02/22604; WO 02/22605; WO 02/22606; WO 02/22607; WO 02/22608; WO 02/50065; WO 02/50066; WO 02/057259; WO 02/059112; WO 02/059111; WO 02/062789; WO 02/066461; WO 02/068415; pyrimidine derivatives: WO 03/077921; WO 03/078423; WO 03/078426; WO 03/078427; WO 04/000833 or imidazole, oxazole and thiazole derivatives: WO 02/96905; WO 04/005283.

Some tricycles or related compounds are known as inhibitors of erythrocyte aggregation from U.S. Pat. No. 4,835,280A, EP 0 189 103, U.S. Pat. No. 4,954,498 and also from Mertens, A., et al., J. Med. Chem. 30 (1987) 1279-1287; von der Saal, W., et al., J. Med. Chem. 32 (1989) 1481-1491; EP 0 318 902; DE 34 17 643; DE 36 42 315 and DE 37 01 277. U.S. Pat. No. 5,212,186A describes related tricycles for the treatment of cardiac insuffiency, hypertension and other diseases.

WO 03/035065 relates to benzimidazole derivatives as kinase inhibitors, especially as inhibitors against kinase insert domain containing receptor (KDR) tyrosine kinase, spleen tyrosine kinase (SYK) and inducible T cell kinase (ITK).

However there remains a need for structural new compounds with improved therapeutic properties, such as enhanced activity, decreased toxicity, better solubility and improved pharmacokinetic profile, to name only a few.

SUMMARY OF THE INVENTION

The present invention relates to the use of the compounds of the general formula I,

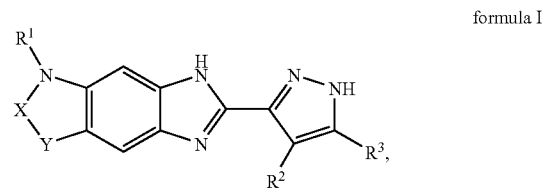

formula I wherein $R^1$, $R^2$, $R^3$, $R^4$, $R^5$, X and Y are as described herewithin below.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as Aurora family kinase inhibitors, especially as Aurora A kinase inhibitors, and may therefore be useful for the treatment of diseases mediated by said kinase. Aurora A inhibition leads to cell cycle arrest in the G2 phase of the cell cycle and exerts an antiproliferative effect in tumor cell lines. This indicates that Aurora A inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas. Treatment of acute-myelogenous leukemia (AML, acute lymphocytic leukemia (ALL) and gastrointestinal stromal tumor (GIST) is included.

DETAILED DESCRIPTION OF THE INVENTION

The present invention relates to the use of the compounds of the general formula I,

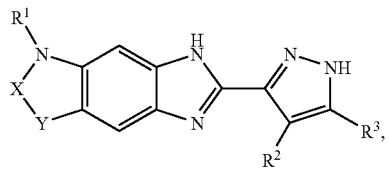

formula I wherein $R^1$ is hydrogen, alkyl or —C(O)-alkyl;

$R^2$ is hydrogen, alkyl, cyano or halogen;

$R^3$ is hydrogen, alkyl, ($C_3$-$C_6$)-cycloalkyl, alkoxy or alkylsulfanyl;

X is —C(O)— or —CH$_2$—;

Y is —NH—, —CH$_2$—CR$^4$R$^5$—, —CR$^4$R$^5$—CH$_2$— or —CR$^4$R$^5$—; wherein $R^4$ is hydrogen or alkyl; and $R^5$ is hydrogen or alkyl, or alternatively $R^4$ and $R^5$ form together with the carbon atom to which they are attached a cycloalkyl ring;

and all their pharmaceutically acceptable salts, for the manufacture of medicaments for the treatment of cancer.

Another embodiment of the invention is the use of the compounds of the formula I, wherein $R^3$ is hydrogen, alkyl or ($C_3$-$C_6$)-cycloalkyl, for the manufacture of medicaments for the treatment of cancer.

Another embodiment of the invention is the use of the compounds of formula I, wherein $R^3$ is hydrogen, alkyl or ($C_3$-$C_6$)-cycloalkyl, as Aurora family kinase inhibitors.

Objects of the present invention are of the compounds of formula I and their tautomers, pharmaceutically acceptable salts, enantiomeric forms, diastereoisomers and racemates, their use as Aurora kinase inhibitors, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

As used herein, the term "alkyl" means a saturated, straight-chain or branched-chain hydrocarbon containing from 1 to 6, preferably 1 or 4, carbon atoms such as methyl, ethyl, n-propyl, isopropyl, n-butyl, 2-butyl, t-butyl. Said alkyl is optionally substituted with one or several halogen atoms, preferably fluorine or chlorine, especially fluorine. Preferably the alkyl is substituted one to five times and more preferably one to three times by such halogen. Examples are trifluoromethyl, 2,2,2-trifluoroethyl, perfluoroethyl and the like, preferably trifluoromethyl. In one embodiment of the invention only the "alkyl" group as used in $R^3$ is optionally substituted by halogen while the other "alkyl" groups as used in $R^1$, $R^2$, $R^4$ and $R^5$ are not substituted by halogen. In another embodiment of the invention all "alkyl" groups are not substituted by halogen.

The term "alkoxy" as used herein means an alkyl group as defined above which is attached via an oxygen atom (alkyl-O—).

The term "alkylsulfanyl" as used herein means an alkyl group as defined above which is attached via an sulfur atom (alkyl-S—).

The term "cycloalkyl" as used herein means a carbocyclic unsaturated ring system containing from 3 to 6, preferably from 3 to 5, carbon atoms. Such carbocyclic unsaturated ring system can be optionally substituted one to three, preferably one or two times, especially one time by alkyl. Examples are cyclopropyl, 1-methyl-cycloprop-1-yl, cyclobutyl, cyclopentyl and cyclohexyl, preferably cyclopropyl. In an embodiment of the invention, the term "cycloalkyl" as used in $R^3$ denotes a cyclopropyl. The cycloalkyl ring which is formed by $R^4$ and $R^5$ together with the carbon atom to which they are attached is preferably a cyclopentyl or cyclohexyl ring, especially a cyclopentyl ring.

The term "halogen" as used herein means fluorine, chlorine, bromine and iodine, preferably fluorine, chlorine or bromine, and more preferred fluorine and chlorine.

The compounds of formula I can exist in different tautomeric forms and in variable mixtures thereof. All tautomeric forms of the compounds of formula I and mixtures thereof are an objective of the invention. For example, the imidazole part of the tricyclic ring system of formula I can exist in two tautomeric forms as shown here below:

formula I

Also, e.g. the pyrazole ring of formula I can form two tautomeric forms as shown here below:

formula I

As used herein, in relation to mass spectrometry (MS) the term "API+" refers to positive atmospheric pressure ionization mode the term "API−" refers to negative atmospheric pressure ionization mode and the term "ESI+" refers to positive electrospray ionization mode.

An embodiment of the invention is the use of the compounds of formula I, wherein X is —CH$_2$—;

for the manufacture of medicaments for the treatment of cancer.

An embodiment of the invention is the use of the compounds of formula I, wherein R$^3$ is hydrogen, alkyl or (C$_3$-C$_6$)-cycloalkyl; and X is —CH$_2$—;

for the manufacture of medicaments for the treatment of cancer.

An embodiment of the invention is the use of the compounds of formula I, wherein X is —CH$_2$—;

as Aurora family kinase inhibitors.

Another embodiment of the invention is the use of the compounds of formula I, wherein X is —CH$_2$—; and Y is —CR$^4$R$^5$—;

for the manufacture of medicaments for the treatment of cancer.

Another embodiment of the invention is the use of the compounds of formula I, wherein R$^3$ is hydrogen, alkyl or (C$_3$-C$_6$)-cycloalkyl;

X is —CH$_2$—; and

Y is —CR$^4$R$^5$—;

for the manufacture of medicaments for the treatment of cancer.

Another embodiment of the invention is the use of the compounds of formula I, wherein X is —CH$_2$—; and Y is —CR$^4$R$^5$—;

as Aurora family kinase inhibitors.

Still another embodiment of the invention is the use of the compounds of formula I, wherein X is —CH$_2$—; and Y is —NH—, —CH$_2$—CR$^4$R$^5$— or —CR$^4$R$^5$—CH$_2$—;

for the manufacture of medicaments for the treatment of cancer.

Still another embodiment of the invention is the use of the compounds of formula I, wherein R$^3$ is hydrogen, alkyl or (C$_3$-C$_6$)-cycloalkyl;

X is —CH$_2$—; and

Y is —NH—, —CH$_2$—CR$^4$R$^5$— or —CR$^4$R$^5$—CH$_2$—;

for the manufacture of medicaments for the treatment of cancer.

Still another embodiment of the invention is the use of the compounds of formula I, wherein X is —CH$_2$—; and Y is —NH—, —CH$_2$—CR$^4$R$^5$— or —CR$^4$R$^5$—CH$_2$—;

as Aurora family kinase inhibitors.

Yet another embodiment of the invention is the use of the compounds of formula I, wherein X is —C(O)—;

for the manufacture of medicaments for the treatment of cancer.

Yet another embodiment of the invention is the use of the compounds of formula I, wherein $R^3$ is hydrogen, alkyl or $(C_3\text{-}C_6)$-cycloalkyl; and X is —C(O)—;

for the manufacture of medicaments for the treatment of cancer.

Yet another embodiment of the invention is the use of the compounds of formula I, wherein X is —C(O)—;

as Aurora family kinase inhibitors.

Another embodiment of the invention is the use of the compounds of formula I, wherein X is —C(O)—; and Y is —CH$_2$—CR$^4$R$^5$— or —CR$^4$R$^5$—CH$_2$—;

for the manufacture of medicaments for the treatment of cancer.

Another embodiment of the invention is the use of the compounds of formula I, wherein $R^3$ is hydrogen, alkyl or $(C_3\text{-}C_6)$-cycloalkyl;

X is —C(O)—; and

Y is —CH$_2$—CR$^4$R$^5$— or —CR$^4$R$^5$—CH$_2$—;

for the manufacture of medicaments for the treatment of cancer.

Another embodiment of the invention is the use of the compounds of formula I, wherein X is —C(O)—; and Y is —CH$_2$—CR$^4$R$^5$— or —CR$^4$R$^5$—CH$_2$—;

as Aurora family kinase inhibitors.

Still another embodiment of the invention is the use of the compounds of formula I, wherein X is —C(O)—; and Y is —NH— or —CR$^4$R$^5$—;

for the manufacture of medicaments for the treatment of cancer.

Still another embodiment of the invention is the use of the compounds of formula I, wherein $R^3$ is hydrogen, alkyl or $(C_3\text{-}C_6)$-cycloalkyl;

X is —C(O)—; and

Y is —NH— or —CR$^4$R$^5$—;

for the manufacture of medicaments for the treatment of cancer.

Still another embodiment of the invention is the use of the compounds of formula I, wherein X is —C(O)—; and Y is —NH— or —CR$^4$R$^5$—;

as Aurora family kinase inhibitors.

Yet another embodiment of the invention is the use of the compounds of formula I, wherein X is —C(O)—; and Y is —CR$^4$R$^5$—;

for the manufacture of medicaments for the treatment of cancer.

Yet another embodiment of the invention is the use of the compounds of formula I, wherein $R^3$ is hydrogen, alkyl or $(C_3\text{-}C_6)$-cycloalkyl;

X is —C(O)—; and

Y is —CR$^4$R$^5$—;

for the manufacture of medicaments for the treatment of cancer.

Yet another embodiment of the invention is the use of the compounds of formula I, wherein X is —C(O)—; and Y is —CR$^4$R$^5$—;

as Aurora family kinase inhibitors.

Another embodiment of the invention is the use of the compounds of formula I, wherein X is —C(O)—; and Y is —NH—;

for the manufacture of medicaments for the treatment of cancer.

Another embodiment of the invention is the use of the compounds of formula I, wherein $R^3$ is hydrogen, alkyl or $(C_3\text{-}C_6)$-cycloalkyl;

X is —C(O)—; and

Y is —NH—;

for the manufacture of medicaments for the treatment of cancer.

Another embodiment of the invention is the use of the compounds of formula I, wherein X is —C(O)—; and Y is —NH—;

as Aurora family kinase inhibitors.

Medicaments containing a compound of the present invention or a pharmaceutically acceptable salt thereof and a therapeutically inert carrier are an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their Aurora tyrosine kinase inhibition and their antiproliferative activity, said compounds are useful for the treatment of diseases such as cancer in humans or animals and for the production of corresponding medicaments. The dosage depends on various factors such as manner of administration, species, age and/or individual state of health.

Another embodiment of the invention is a medicament containing one or more compounds of formula I as active ingredients together with pharmaceutically acceptable adjuvants for the treatment of diseases mediated by an inappropriate activation of Aurora family tyrosine kinases, especially Aurora A tyrosine kinase.

Another embodiment of the invention is a medicament containing one or more compounds of formula I as active ingredients together with pharmaceutically acceptable adjuvants for the treatment of cancer.

Another embodiment of the invention is a medicament containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a medicament containing one or more compounds of formula I as active ingredients together with pharmaceutically acceptable adjuvants for the treatment of acute-myelogenous leukemia (AML, acute lymphocytic leukemia (ALL) and gastrointestinal stromal tumor (GIST).

Another embodiment of the invention is the use of one or more compounds of formula I for the manufacture of medicaments for the treatment of diseases mediated by an inappropriate activation of Aurora family tyrosine kinases.

Another embodiment of the invention is the use of the compounds of formula I as Aurora A tyrosine kinase inhibitors.

Another embodiment of the invention is the use of the compounds of formula I as anti-proliferating agents.

Another embodiment of the invention is the use of one or more compounds of formula I for the treatment of cancer.

Another embodiment of the invention is the use of one or more compounds of formula I for the manufacture of medicaments for the treatment of diseases mediated by an inappropriate activation of Aurora family tyrosine kinases.

Another embodiment of the invention is the use of one or more compounds of formula I for the manufacture of medicaments for the treatment for the treatment of cancer.

Another embodiment of the invention is the use of one or more compounds of formula I for the manufacture of medicaments for the treatment of colorectal, breast, lung, prostate, pancreatic, gastric, bladder, ovarian, melanoma, neuroblastoma, cervical, kidney or renal cancers, leukemias or lymphomas Another embodiment of the invention is the use of one or more compounds of formula I for the manufacture of medicaments for the treatment of acute-myelogenous leukemia (AML, acute lymphocytic leukemia (ALL) and gastrointestinal stromal tumor (GIST). Another embodiment of the invention is a medicament containing one or more compounds of formula I as active ingredients together with pharmaceutically acceptable adjuvants for the treatment of diseases mediated by an inappropriate activation of Aurora family tyrosine kinases, especially Aurora A tyrosine kinase.

Another embodiment of the invention is a medicament containing one or more compounds of formula I as active ingredients together with pharmaceutically acceptable adjuvants for the treatment of cancer.

Another embodiment of the invention is a medicament containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a medicament containing one or more compounds of formula I as active ingredients together with pharmaceutically acceptable adjuvants for the treatment of acute-myelogenous leukemia (AML, acute lymphocytic leukemia (ALL) and gastrointestinal stromal tumor (GIST).

Another embodiment of the invention are the compounds of formula I, wherein $R^3$ is hydrogen, alkyl or $(C_3-C_6)$-cycloalkyl; and X is —$CH_2$—.

Still another embodiment of the invention are the compounds of formula I, wherein $R^3$ is hydrogen, alkyl or $(C_3-C_6)$-cycloalkyl;

X is —$CH_2$—; and

Y is —$CR^4R^5$—.

Such compounds are for example:

7,7-Dimethyl-2-(5-methyl-2H-pyrazol-3-yl)-3,5,6,7-tetrahydro-imidazo[4,5-f]indole; and 1-[7,7-Dimethyl-2-(5-methyl-2H-pyrazol-3-yl)-6,7-dihydro-3H-imidazo[4,5-f]indol-5-yl]-ethanone.

Another embodiment of the invention are the compounds of formula I, wherein $R^3$ is hydrogen, alkyl or $(C_3-C_6)$-cycloalkyl;

X is —$CH_2$—; and

Y is —NH—, —$CH_2$—$CR^4R^5$— or —$CR^4R^5$—$CH_2$—.

Another embodiment of the invention are the compounds of formula I, wherein $R^3$ is hydrogen, alkyl or $(C_3-C_6)$-cycloalkyl;

X is —C(O)—; and

Y is —NH—.

Such compounds are for example:

6-(5-Methyl-1H-pyrazol-3-yl)-3,5-dihydro-1H-benzo[1,2-d;4,5-d']diimidazol-2-one;

3-Methyl-6-(5-methyl-1H-pyrazol-3-yl)-3,5-dihydro-1H-benzo[1,2-d;4,5-d']diimidazol-2-one; and 3-Isopropyl-6-(5-methyl-1H-pyrazol-3-yl)-3,5-dihydro-1H-benzo[1,2-d;4,5-d']diimidazol-2-one.

A preferred embodiment of the invention are the compounds of formula I, wherein $R^1$ is alkyl or —C(O)-alkyl.

Another preferred embodiment of the invention are the compounds of formula I, wherein $R^1$ is alkyl.

Another preferred embodiment of the invention are the compounds of formula I, wherein $R^1$ is alkyl; and $R^2$ is hydrogen or alkyl.

Another preferred embodiment of the invention are the compounds of formula I, wherein $R^1$ is alkyl;

$R^2$ is hydrogen or alkyl; and $R^3$ is hydrogen, alkyl or $(C_3\text{-}C_6)$-cycloalkyl.

Another preferred embodiment of the invention are the compounds of formula I, wherein $R^1$ is alkyl;

X is —C(O)—; and

Y is —CH$_2$—CR$^4$R$^5$—, —CR$^4$R$^5$—CH$_2$— or —CR$^4$R$^5$—.

Another preferred embodiment of the invention are the compounds of formula I, wherein $R^1$ is alkyl;

$R^3$ is hydrogen, alkyl or $(C_3\text{-}C_6)$-cycloalkyl;

X is —C(O)—; and

Y is —CH$_2$—CR$^4$R$^5$—, —CR$^4$R$^5$—CH$_2$— or —CR$^4$R$^5$—.

Another preferred embodiment of the invention are the compounds of formula I, wherein $R^1$ is alkyl;

$R^2$ is hydrogen or alkyl;

X is —C(O)—; and

Y is —CR$^4$R$^5$—.

Another preferred embodiment of the invention are the compounds of formula I, wherein $R^1$ is alkyl;

$R^2$ is hydrogen;

$R^3$ is hydrogen, alkyl or $(C_3\text{-}C_6)$-cycloalkyl;

X is —C(O)—; and

Y is —CR$^4$R$^5$—.

Such compounds are for example:

5-Ethyl-7,7-dimethyl-2-(5-methyl-1H-pyrazol-3-yl)-5,7-dihydro-3H-imidazo[4,5-f]indol-6-one;

5-Ethyl-7,7-dimethyl-2-(5-propyl-2H-pyrazol-3-yl)-5,7-dihydro-3H-imidazo[4,5-f]indol-6-one;

5,7,7-Trimethyl-2-(5-propyl-2H-pyrazol-3-yl)-5,7-dihydro-3H-imidazo[4,5-f]indol-6-one;

5-Ethyl-2-(5-isobutyl-2H-pyrazol-3-yl)-7,7-dimethyl-5,7-dihydro-3H-imidazo[4,5-f]indol-6-one;

2-(5-Isobutyl-2H-pyrazol-3-yl)-5,7,7-trimethyl-5,7-dihydro-3H-imidazo[4,5-f]indol-6-one;

5,7,7-Trimethyl-2-(1H-pyrazol-3-yl)-5,7-dihydro-3H-imidazo[4,5-f]indol-6-one;

5,7,7-Trimethyl-2-(5-methyl-1H-pyrazol-3-yl)-5,7-dihydro-3H-imidazo[4,5-f]indol-6-one;

5-Ethyl-7,7-dimethyl-2-(1H-pyrazol-3-yl)-5,7-dihydro-3H-imidazo[4,5-f]indol-6-one;

5-Ethyl-7,7-dimethyl-2-(5-propyl-2H-pyrazol-3-yl)-5,7-dihydro-3H-imidazo[4,5-f]indol-6-one; compound with acetic acid;

5-Isopropyl-7,7-dimethyl-2-(5-methyl-2H-pyrazol-3-yl)-5,7-dihydro-1H-imidazo[4,5-f]indol-6-one;

5-Isopropyl-7,7-dimethyl-2-(5-propyl-2H-pyrazol-3-yl)-5,7-dihydro-1H-imidazo[4,5-f]indol-6-one;

7,7-Dimethyl-2-(5-methyl-2H-pyrazol-3-yl)-5-propyl-5,7-dihydro-1H-imidazo[4,5-f]indol-6-one; and 7,7-Dimethyl-5-propyl-2-(5-propyl-2H-pyrazol-3-yl)-5,7-dihydro-3H-imidazo[4,5-f]indol-6-one.

Another preferred embodiment of the invention are the compounds of formula I, wherein $R^1$ is alkyl;

$R^2$ is hydrogen or alkyl;

$R^3$ is alkyl which is substituted one or several times by halogen;

X is —C(O)—; and

Y is —CR$^4$R$^5$—.

Such compounds are for example:

5-Ethyl-7,7-dimethyl-2-(5-trifluoromethyl-1H-pyrazol-3-yl)-5,7-dihydro-3H-imidazo[4,5-f]indol-6-one;

5-Isopropyl-7,7-dimethyl-2-(5-trifluoromethyl-2H-pyrazol-3-yl)-5,7-dihydro-1H-imidazo[4,5-f]indol-6-one;

7,7-Dimethyl-5-propyl-2-(5-trifluoromethyl-2H-pyrazol-3-yl)-5,7-dihydro-1H-imidazo[4,5-f]indol-6-one; and 5,7,7-Trimethyl-2-(5-trifluoromethyl-2H-pyrazol-3-yl)-5,7-dihydro-3H-imidazo[4,5-f]indol-6-one.

Another preferred embodiment of the invention are the compounds of formula I, wherein $R^1$ is alkyl;

$R^2$ is hydrogen or alkyl;

$R^3$ is alkoxy or alkylsulfanyl;

X is —C(O)—; and

Y is —CR$^4$R$^5$—.

Such compounds are for example:

5-Ethyl-2-(5-methoxy-1H-pyrazol-3-yl)-7,7-dimethyl-5,7-dihydro-3H-imidazo[4,5-f]indol-6-one; and 5-Ethyl-7,7-dimethyl-2-(5-methylsulfanyl-1H-pyrazol-3-yl)-5,7-dihydro-1H-imidazo[4,5-f]indol-6-one Another preferred embodiment of the invention are the compounds of formula I, wherein $R^1$ is alkyl;

$R^2$ is hydrogen or alkyl;

$R^3$ is hydrogen, alkyl or $(C_3\text{-}C_6)$-cycloalkyl;

X is —C(O)—; and

Y is —CH$_2$—CR$^4$R$^5$— or —CR$^4$R$^5$—CH$_2$—.

Another preferred embodiment of the invention are the compounds of formula I, wherein $R^1$ is alkyl;

$R^2$ is hydrogen or alkyl;

$R^3$ is hydrogen, alkyl or $(C_3\text{-}C_6)$-cycloalkyl;

X is —C(O)—; and

Y is —NH—.

Such compounds are for example:

3-Methyl-6-(5-methyl-1H-pyrazol-3-yl)-3,5-dihydro-1H-benzo[1,2-d;4,5-d']diimidizol-2-one; and 3-Isopropyl-6-(5-methyl-1H-pyrazol-3-yl)-3,5-dihydro-1H-benzo[1,2-d;4,5-d']diimidazol-2-one.

Another preferred embodiment of the invention are the compounds of formula I, wherein $R^1$ is —C(O)-alkyl;

$R^2$ is hydrogen or alkyl;

$R^3$ is hydrogen, alkyl or $(C_3-C_6)$-cycloalkyl;

X is —CH$_2$—; and

Y is —CH$_2$—CR$^4$R$^5$—, —CR$^4$R$^5$—CH$_2$— or —CR$^4$R$^5$—.

Such a compound is for example:

1-[7,7-Dimethyl-2-(5-methyl-2H-pyrazol-3-yl)-6,7-dihydro-3H-imidazo[4,5-f]indol-5-yl]-ethanone.

Another embodiment of the invention is a medicament containing one or more compounds of formula I, with the proviso that, if $R^1$ and $R^2$ are hydrogen, X is —C(O)— and Y is —CR$^4$R$^5$—; wherein $R^4$ and $R^5$ are methyl; then $R^3$ is hydrogen, $(C_2-C_6)$alkyl or $(C_3-C_6)$-cycloalkyl, as active ingredients together with pharmaceutically acceptable adjuvants Another embodiment of the invention is a medicament containing one or more compounds of formula I, wherein $R^3$ is hydrogen, $(C_2-C_6)$alkyl, $(C_3-C_6)$-cycloalkyl or fluorine, as active ingredients together with pharmaceutically acceptable adjuvants Another embodiment of the invention is a medicament containing one or more compounds of formula I, wherein $R^1$ is alkyl or —C(O)-alkyl, as active ingredients together with pharmaceutically acceptable adjuvants.

Another embodiment of the invention is a medicament containing one or more compounds of formula I, wherein $R^1$ is alkyl, as active ingredients together with pharmaceutically acceptable adjuvants.

Another embodiment of the invention is the use of one of the following compounds for the manufacture of a medicament for the treatment of cancer:

7,7-Dimethyl-2-(5-methyl-2H-pyrazol-3-yl)-3,5,6,7-tetrahydro-imidazo[4,5-f]indole;

1-[7,7-Dimethyl-2-(5-methyl-2H-pyrazol-3-yl)-6,7-dihydro-3H-imidazo[4,5-f]indol-5-yl]-ethanone;

8,8-Dimethyl-2-(5-methyl-1H-pyrazol-3-yl)-1,5,7,8-tetrahydro-imidazo[4,5-g]quinolin-6-one;

2-(5-Isobutyl-2H-pyrazol-3-yl)-8,8-dimethyl-1,5,7,8-tetrahydro-imidazo[4,5-g]quinolin-6-one;

7,7-Dimethyl-2-(5-methyl-2H-pyrazol-3-yl)-5,7-dihydro-1H-imidazo[4,5-f]indol-6-one;

2-(5-Isobutyl-2H-pyrazol-3-yl)-7,7-dimethyl-5,7-dihydro-1H-imidazo[4,5-f]indol-6-one;

2-(5-methyl-2H-pyrazol-3-yl)-spiro[7,7-cyclopentan-5,7-dihydro-3H-imidazo[4,5-f]indol]-6-one; or according to actual IUPAC nomenclature 2-(5-methyl-2H-pyrazol-3-yl)-spiro-5,7-dihydro[cyclopentane-1',7-imidazo[4,5-f]indol]-6(3H)-one;

2-(5-Isobutyl-2H-pyrazol-3-yl)-spiro[7,7-cyclopentan-5,7-dihydro-1H-imidazo[4,5-f]indol]-6-one; or according to actual IUPAC nomenclature 2-(5-Isobutyl-2H-pyrazol-3-yl)-spiro-5,7-dihydro[cyclopentane-1',7-imidazo[4,5-f]indol]-6(3H)-one;

6-(5-Methyl-1H-pyrazol-3-yl)-3,5-dihydro-1H-benzo[1,2-d;4,5-d']diimidazol-2-one;

2-(4,5-Dimethyl-1H-pyrazol-3-yl)-7,7-dimethyl-5,7-dihydro-1H-imidazo[4,5-f]indol-6-one;

7,7-Dimethyl-2-[5-(3-methyl-butyl)-1H-pyrazol-3-yl]-5,7-dihydro-1H-imidazo[4,5-f]indol-6-one;

2-(5-Ethyl-4-methyl-1H-pyrazol-3-yl)-7,7-dimethyl-5,7-dihydro-1H-imidazo[4,5-f]indol-6-one;

7,7-Dimethyl-2-(1H-pyrazol-3-yl)-5,7-dihydro-1H-imidazo[4,5-f]indol-6-one;

2-(5-Cyclopropyl-1H-pyrazol-3-yl)-7,7-dimethyl-5,7-dihydro-1H-imidazo[4,5-f]indol-6-one;

2-(5-Isopropyl-2H-pyrazol-3-yl)-7,7-dimethyl-5,7-dihydro-1H-imidazo[4,5-f]indol-6-one;

8,8-Dimethyl-2-(5-propyl-2H-pyrazol-3-yl)-1,5,7,8-tetrahydro-imidazo[4,5-g]quinolin-6-one;

8,8-Dimethyl-2-(1H-pyrazol-3-yl)-1,5,7,8-tetrahydro-imidazo[4,5-g]quinolin-6-one;

2-(5-Cyclopropyl-1H-pyrazol-3-yl)-8,8-dimethyl-1,5,7,8-tetrahydro-imidazo[4,5-g]quinolin-6-one 2-(5-Isopropyl-2H-pyrazol-3-yl)-8,8-dimethyl-1,5,7,8-tetrahydro-imidazo[4,5-g]quinolin-6-one;

2-(2H-pyrazol-3-yl)-spiro-5,7-dihydro[cyclopentane-1',7-imidazo[4,5-f]indol]-6(3H)-one;

2-(5-Isopropyl-2H-pyrazol-3-yl)-spiro-5,7-dihydro[cyclopentane-1',7-imidazo[4,5-f]indol]-6(3H)-one;

2-(5-Propyl-2H-pyrazol-3-yl)-spiro-5,7-dihydro[cyclopentane-1',7-imidazo[4,5-f]indol]-6(3H)-one;

7,7-Dimethyl-2-(5-trifluoromethyl-2H-pyrazol-3-yl)-5,7-dihydro-1H-imidazo[4,5-f]indol-6-one; and 2-(5-Cyclopropyl-2H-pyrazol-3-yl)-spiro-5,7-dihydro[cyclopentane-1',7-imidazo[4,5-f]indol]-6(3H)-one.

Another embodiment of the invention is the use of one of the following compounds for the manufacture of a medicament for the treatment of cancer:

3-Methyl-6-(5-methyl-1H-pyrazol-3-yl)-3,5-dihydro-1H-benzo[1,2-d;4,5-d']diimidazol-2-one;

3-Isopropyl-6-(5-methyl-1H-pyrazol-3-yl)-3,5-dihydro-1H-benzo[1,2-d;4,5-d']diimidazol-2-one;

5-Ethyl-7,7-dimethyl-2-(5-methyl-1H-pyrazol-3-yl)-5,7-dihydro-3H-imidazo[4,5-f]indol-6-one;

5-Ethyl-7,7-dimethyl-2-(5-propyl-2H-pyrazol-3-yl)-5,7-dihydro-3H-imidazo[4,5-f]indol-6-one;

5,7,7-Trimethyl-2-(5-propyl-2H-pyrazol-3-yl)-5,7-dihydro-3H-imidazo[4,5-f]indol-6-one;

5-Ethyl-2-(5-isobutyl-2H-pyrazol-3-yl)-7,7-dimethyl-5,7-dihydro-3H-imidazo[4,5-f]-one;

2-(5-Isobutyl-2H-pyrazol-3-yl)-5,7,7-trimethyl-5,7-dihydro-3H-imidazo[4,5-f]indol-6-one;

5,7,7-Trimethyl-2-(1H-pyrazol-3-yl)-5,7-dihydro-3H-imidazo[4,5-f]indol-6-one;

5,7,7-Trimethyl-2-(5-methyl-1H-pyrazol-3-yl)-5,7-dihydro-3H-imidazo[4,5-f]indol-6-one;

5-Ethyl-7,7-Trimethyl-2-(1H-pyrazol-3-yl)-5,7-dihydro-3H-imidazo[4,5-f]indol-6-one;

5-Ethyl-7,7-dimethyl-2-(5-propyl-2H-pyrazol-3-yl)-5,7-dihydro-3H-imidazo[4,5-f]indol-6-one; compound with acetic acid;

5-Isopropyl-7,7-dimethyl-2-(5-methyl-2H-pyrazol-3-yl)-5,7-dihydro-1H-imidazo[4,5-f]indol-6-one;

5-Isopropyl-7,7-dimethyl-2-(5-propyl-2H-pyrazol-3-yl)-5,7-dihydro-1H-imidazo[4,5-f]indol-6-one;

7,7-Dimethyl-2-(5-methyl-2H-pyrazol-3-yl)-5-propyl-5,7-dihydro-1H-imidazo[4,5-f]indol-6-one;

7,7-Dimethyl-5-propyl-2-(5-propyl-2H-pyrazol-3-yl)-5,7-dihydro-3H-imidazo[4,5-f]indol-6-one;

5-Ethyl-7,7-dimethyl-2-(5-trifluoromethyl-1H-pyrazol-3-yl)-5,7-dihydro-3H-imidazo[4,5-f]indol-6-one;

5-Isopropyl-7,7-dimethyl-2-(5-trifluoromethyl-2H-pyrazol-3-yl)-5,7-dihydro-1H-imidazo[4,5-f]indol-6-one;

7,7-Dimethyl-5-propyl-2-(5-trifluoromethyl-2H-pyrazol-3-yl)-5,7-dihydro-1H-imidazo[4,5-f]indol-6-one;

5,7,7-Trimethyl-2-(5-trifluoromethyl-2H-pyrazol-3-yl)-5,7-dihydro-3H-imidazo[4,5-f]indol-6-one;

5-Ethyl-2-(5-methoxy-1H-pyrazol-3-yl)-7,7-dimethyl-5,7-dihydro-3H-imidazo[4,5-f]indol-6-one; and 5-Ethyl-7,7-dimethyl-2-(5-methylsulfanyl-1H-pyrazol-3-yl)-5,7-dihydro-1H-imidazo[4,5-f]indol-6-one;

Another embodiment of the invention is a process for the preparation of the compounds of formula I, wherein $R^1$ is alkyl or —C(O)-alkyl;

by reacting a compound of formula II

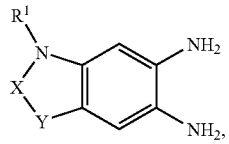

formula II wherein $R^1$ is alkyl or —C(O)-alkyl and X and Y have the significance given above for formula I;
with a compound of formula III,

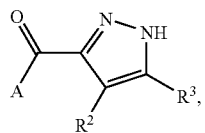

formula III wherein A is —OH, —Cl, —H or —OMe and $R^2$ and $R^3$ have the significance given above for formula I;
to give the compounds of formula I,

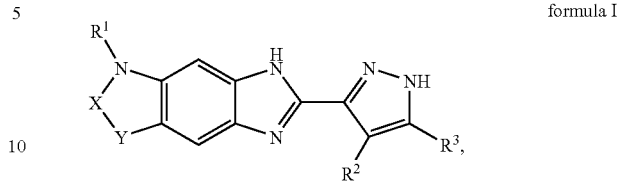

formula I wherein $R^1$ is alkyl or —C(O)-alkyl and $R^2$, $R^3$, X and Y have the
significance given above for formula I;

isolating said compound of formula I from the reaction mixture, and if desired, converting it into a pharmaceutically acceptable salt.

The compounds of formula I, or a pharmaceutically acceptable salt thereof, which are subject of the present invention may be prepared by any process known to be applicable to the preparation of chemically-related compounds. Such processes, when used to prepare a compound of the formula I, or a pharmaceutically-acceptable salt thereof, are illustrated by the following representative schemes 1 and 2 and examples in which, unless otherwise stated, X, Y, $R^1$, $R^2$ and $R^3$ have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

The benzimidazole ring system of formula I can be formed by different synthetic pathways in analogy to methods described in the literature (Mertens, A., et al., J. Med. Chem. 30 (1987) 1279-1287; DE 35 31 678).

One route for the preparation of compounds of formula I (Scheme 1) starts from diamines of formula II which can be reacted with carboxylic acids (compounds of formula III wherein A is OH), acid chlorides (A is Cl), aldehydes (A is H), methyl carboxylates (A is OMe) or activated esters (A is e.g. hydroxybenzotriazole). For detailed procedures see the literature cited above.

Scheme 1

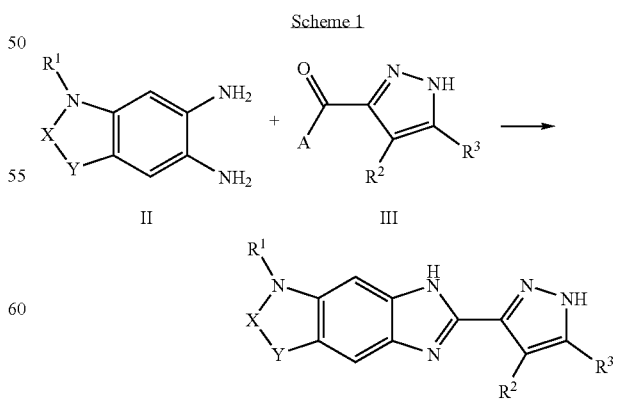

Pyrazoles of formula III are commercially available or they can be prepared by standard procedures of organic chemistry (see e.g. Stanovnik, B., and Svete, J., Science of Synthesis 12 (2002) 15-225), e.g. condensation of a 1,3-dicarbonyl compound with hydrazine (see e.g. WO 04/032928 or van Herk, T., et al., J. Med. Chem. 46 (2003) 3945-3951) or 1,3-dipolar cycloaddition between a diazo compound and an acetylene (see e.g. Sewald, N., et al., Liebigs Ann. Chem. (1992) 947-952). Pyrazoles of formula III wherein $R^3$ is alkoxy can be prepared either via the 5-hydroxy-pyrazole-3-carboxylic acid esters (see e.g. Ochi, H. et al., Chem. Pharm. Bull. 31 (1983) 1228-1234) with subsequent O-alkylation of the 5-hydroxy group with alkylhalogenides in the presence of a base such as caesium carbonate and the like in solvents such as dimethylformamide (DMF), N-methyl-pyrrolidinone (NMP) and the like (see e.g. WO 03/035065) or according to the procedure of Martins, M. A. P., et al., Synthesis 15 (2003) 2353-2357. And pyrazoles of formula III wherein $R^3$ is alkylsulfanyl can be prepared via the corresponding oxo-ketene dithioacetals according to Mahata, P. K., et al., Tetrahedron 59 (2003) 2631-2639. Alternatively to Scheme 1, the 5-alkoxy- or 5-alkylsulfanyl-pyrazole moieties of compounds of formula I, wherein $R^3$ is alkoxy or alkylsulfanyl, can be introduced by another sequence of reaction steps as described in WO 03/035065. Pyrazoles of formula III wherein $R^2$ is hydrogen, $R^3$ is trifluoromethyl and A is hydroxy can be prepared in a three step procedure according to Scheme 1a: condensation of 4,4,4-trifluoro-1-(2-furyl)-1,3-butanedione with benzyl hydrazine under acidic conditions, oxidative degradation of the furan ring with potassium permanganate to the carboxylic acid functionality (see e.g. Djuric, S. W., et al., J. Med. Chem. 43 (2000) 2975-2981; Jia, Z. J., et al., Bioorg. Med. Chem. Lett. 12 (2002) 1651-1655 or Pruitt, J. R., et al., J. Med. Chem. 46 (2003) 5298-5315) and cleavage of the benzyl protecting group provides the desired 5-trifluoromethyl-2H-pyrazole-3-carboxylic acid.

Scheme 1a

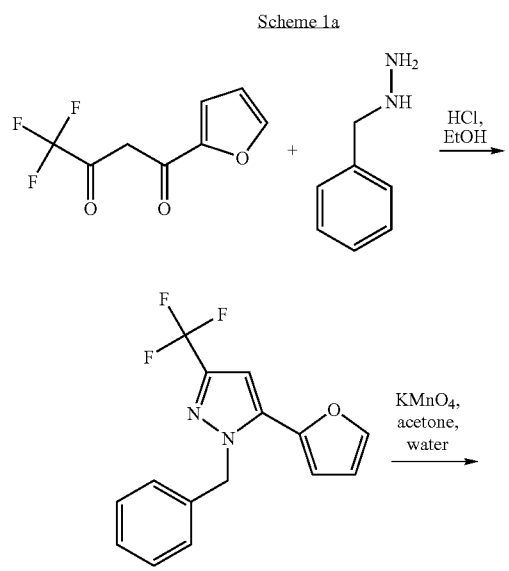

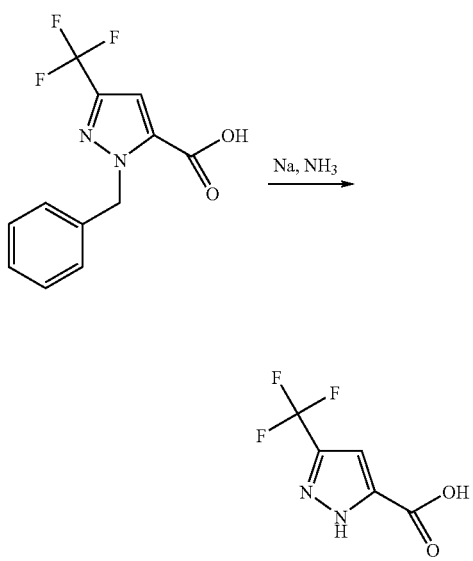

This procedure involving the N-benzyl or alternatively the p-methoxybenzyl group (Subramanyam, C., Synth. Commun. 25 (1995) 761-774 as intermediate protecting group can be also applied for preparing other pyrazoles needed as starting material.

Compounds of formula II wherein X is —C(O)—, $R^1$ is hydrogen or alkyl and Y is —CR$^4$R$^5$ or —NH— can be prepared in an analogous manner as described in Mertens, A., et al., J. Med. Chem. 30 (1987) 1279-1287; von der Saal, W., et al., J. Med. Chem. 32 (1989) 1481-1491; DE 34 17 643; EP 0 318 902, U.S. Pat. No. 4,666,923A, U.S. Pat. No. 4,695,567A, U.S. Pat. No. 4,863,945A and U.S. Pat. No. 4,985,448A. Compounds of formula II wherein X is —C(O)— or —CH$_2$—, $R^1$ is hydrogen or —C(O)alkyl and Y is —CR$^4$R$^5$— can be prepared according to DE 36 42 315. And furthermore the compounds of formula II wherein X is —C(O)— or —CH$_2$—, $R^1$ is hydrogen or alkyl and Y is —CR$^4$R$^5$—CH$_2$— or —CH$_2$—CR$^4$R$^5$— are described in DE 37 01 277.

For instance, the diamines of formula II, wherein X is —C(O)—, $R^1$ is hydrogen or alkyl and Y is —CR$^4$R$^5$, are named IIa and can be synthesized according to U.S. Pat. No. 4,666,923A, DE 34 10 168 and Mertens, A., et al., J. Med. Chem. 30 (1987) 1279-1287 as shown in Scheme 1b:

Scheme 1b

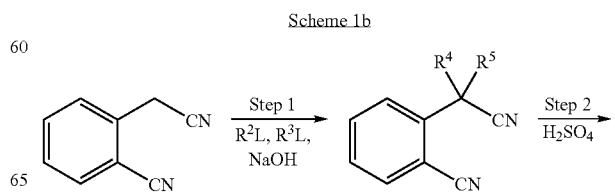

-continued

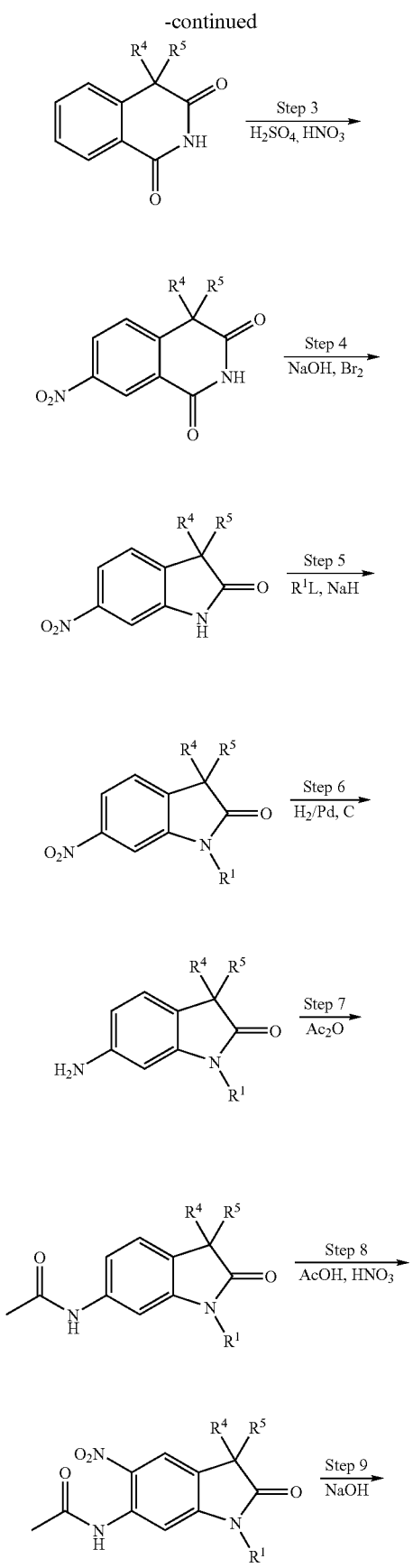

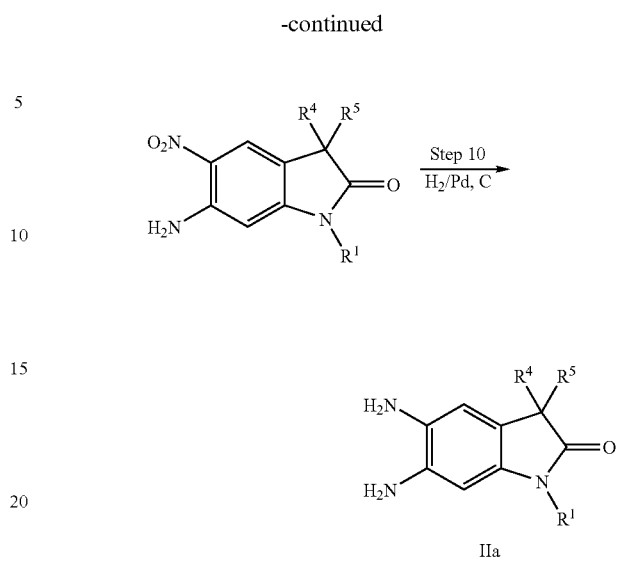

In scheme 1b, $R^1$, $R^4$ and $R^5$ have the significance as given above for formula I and L represents a leaving group as e.g. iodine, bromine, chlorine, triflate and the like.

In an alternative procedure diamines of formula IIa, wherein $R^1$ is alkyl, can be obtained by an alkylation of diamines of formula IIb (compounds II wherein X is —C(O)—, $R^1$ is hydrogen and Y is —$CR^4R^5$,) as shown in scheme 1c.

Scheme 1c

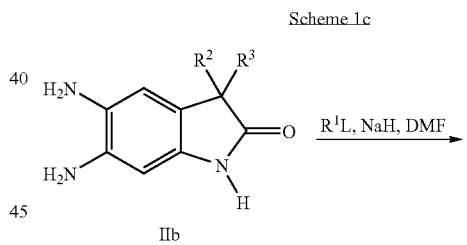

Diamines of formula IIb can be synthesized according to scheme 1b under omission of step 5.

Another synthesis of compounds of formula I (Scheme 2) starts from nitro-compounds IV or V which are hydrogenated and subsequently cyclized with acetic acid or hydrochloric acid to the desired benzimidazole derivative. For detailed procedures see Mertens, A., et al., J. Med. Chem. 30 (1987) 1279-1287; DE 35 31 678.

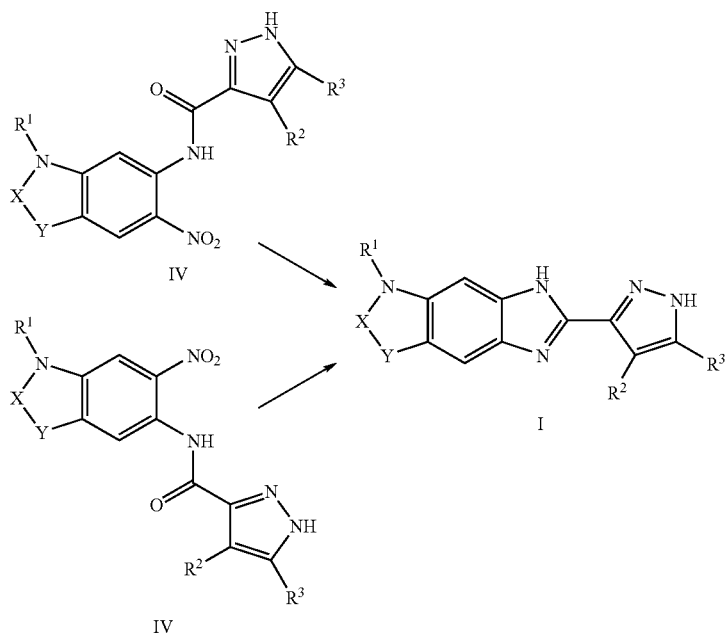

Scheme 2

Compounds of formulas IV and V wherein X is C(O), $R^1$ is hydrogen or alkyl and Y is —$CR^4R^5$, —NH— can be prepared in an analogous manner as described in Mertens, A., et al., J. Med. Chem. 30 (1987) 1279-1287; von der Saal, W., et al., J. Med. Chem. 32 (1989) 1481-1491; DE 34 17 643; EP 0 318 902. Compounds of formulas IV and V with wherein X is C(O) or —$CH_2$—, $R^1$ is hydrogen or —C(O) alkyl and Y is —$CR^4R^5$— can be prepared according to DE 36 42 315. And furthermore the compounds of formula II wherein X is C(O) or —$CH_2$—, $R^1$ is hydrogen or alkyl and Y is —$CR^4R^5$—$CH_2$— or —$CH_2$—$CR^4R^5$— are described in DE 37 01 277.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA) Zürich, (2002) or Bastin, R. J., et al., Organic Proc. Res. Dev. 4 (2000) 427-435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

The compounds of formula I and their pharmaceutically acceptable salts possess valuable pharmacological properties. It has been found that said compounds show activity as inhibitors of the Aurora kinase family and also show antiproliferative activity. Consequently the compounds of the present invention are useful in the therapy and/or prevention of illnesses with known over-expression of kinases of the Aurora family preferably Aurora A, especially in the therapy and/or prevention of illnesses mentioned above. The activity of the present compounds as inhibitors of the Aurora kinase family is demonstrated by the following biological assay:

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

A pharmaceutical compositions comprise e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |

-continued

| Item | Ingredients | mg/tablet | | | |
|------|-------------|-----|-----|-----|-----|
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
Mix items 1, 2, 3 and 4 and granulate with purified water.
Dry the granules at 50° C.
Pass the granules through suitable milling equipment.
Add item 5 and mix for three minutes; compress on a suitable press.

b) Capsule Formulation:

| Item | Ingredients | mg/capsule | | | |
|------|-------------|-----|-----|-----|-----|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
Mix items 1, 2 and 3 in a suitable mixer for 30 minutes.
Add items 4 and 5 and mix for 3 minutes.
Fill into a suitable capsule.

c) Micro Suspension

1. Weigh 4.0 g glass beads in custom made tube GL 25, 4 cm (the beads fill half of the tube).

2. Add 50 mg compound, disperse with spatulum and vortex.

3. Add 2 ml gelatin solution (weight beads: gelatin solution=2:1) and vortex.

4. Cap and wrap in aluminum foil for light protection.

5. Prepare a counter balance for the mill.

6. Mill for 4 hours, 20/s in a Retsch mill (for some substances up to 24 hours at 30/s).

7. Extract suspension from beads with two layers of filter (100 μm) on a filter holder, coupled to a recipient vial by centrifugation at 400 g for 2 min.

8. Move extract to measuring cylinder.

9. Repeat washing with small volumes (here 1 ml steps) until final volume is reached or extract is clear.

10. Fill up to final volume with gelatin and homogenize.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The following examples and references are provided to aid the understanding of the present invention, the true scope of which is set forth in the appended claims. It is understood that modifications can be made in the procedures set forth without departing from the spirit of the invention.

EXAMPLES

A: Starting Materials

Preparation of 5,6-diamino-1-ethyl-3,3-dimethyl-1,3-dihydro-indol-2-one

1-Ethyl-3,3-dimethyl-6-nitro-1,3-dihydro-indol-2-one

A solution of 3,3-dimethyl-6-nitro-1,3-dihydro-indol-2-one (6 g, 29.10 mmol) in anhydrous N,N-dimethylformamide (DMF) (35 ml) was treated with sodium hydride. The resulting suspension was stirred for 1 h at 60° C. A solution of bromo-ethane (2.17 mL, 3.17 g, 29.10 mmol) in DMF (10 ml) was added. The mixture was allowed to cool to room temperature and stirred for 1 h. After removal of the solvent the mixture was quenched with water (100 ml) and extracted with ethyl acetate (3×100 ml). The extract was dried over $Na_2SO_4$, evaporated and the crude product was purified by column chromatography on silica gel. Elution with ethyl acetate/n-heptane (1:3) yielded 5.94 g (87%) of a yellow solid.

MS: M=235.3 (ESI+)
$^1$H-NMR (400 MHz, DMSO): δ (ppm)=1.16 (t, 3H), 1.32 (s, 6H), 3.81 (q, 2H), 7.66 (d, 1H), 7.86 (s, 1H), 7.97 (d, 1H)

6-Amino-1-ethyl-3,3-dimethyl-1,3-dihydro-indol-2-one

To a solution of 1-ethyl-3,3-dimethyl-6-nitro-1,3-dihydro-indol-2-one (5.9 g, 25.19 mmol) in methanol/tetrahydrofuran (THF) (1:1, 80 ml) palladium on charcoal (10%, 1.2 g) was added and the mixture hydrogenated at room temperature for 4 h. After filtration and evaporation of the solvents 5.05 g (98%) 6-amino-1-ethyl-3,3-dimethyl-1,3-dihydro-indol-2-one was isolated as white solid.

MS: M=205.0 (API+)
$^1$H-NMR (400 MHz, DMSO): δ (ppm)=1.11 (t, 3H), 1.17 (s, 6H), 3.58 (q, 2H), 5.12 (br, 2H), 6.21 (d, 1H), 6.25 (s, 1H), 6.92 (d, 1H)

N-(1-Ethyl-3,3-dimethyl-2-oxo-2,3-dihydro-1H-indol-6-yl)-acetamide

A solution of 6-amino-1-ethyl-3,3-dimethyl-1,3-dihydro-indol-2-one (5.05 g, 24.72 mmol) in acetic anhydride (80 ml) was stirred at room temperature for 4 h. The mixture was poured onto ice water (150 ml), allowed to warm to room temperature and was stirred again for 2 h. After extraction with ethyl acetate (3×100 ml), the combined organic layers were washed with sat. $NaHCO_3$-solution (3×100 ml), brine (100 ml) and dried over sodium sulfate. After removal of the solvent the crude product was purified by column chromatography on silica gel (ethyl acetate/n-heptane 1:1) yielding 5.6 g (91%) N-(1-ethyl-3,3-dimethyl-2-oxo-2,3-dihydro-1H-indol-6-yl)-acetamide as light yellow solid.

MS: M=247.1 (API+)

$^1$H-NMR (400 MHz, DMSO): δ (ppm)=1.13 (t, 3H), 1.23 (s, 6H), 2.04 (s, 3H), 3.63 (q, 2H), 7.12 (d, 1H), 7.23 (d, 1H), 7.37 (s, 1H), 9.97 (br, 1H)

N-(1-ethyl-3,3-dimethyl-5-nitro-2-oxo-2,3-dihydro-1H-indol-6-yl)-acetamide

To a solution of N-(1-ethyl-3,3-dimethyl-2-oxo-2,3-dihydro-1H-indol-6-yl)-acetamide (5.6 g, 22.73 mmol) in acetic anhydride (70 ml) nitric acid (100%, 1.96 g, 1.29 ml, 31.2 mmol) was added at 0° C. The mixture was stirred for 30 min, then poured onto ice water (150 ml). After stirring for 4 h the mixture was extracted with ethyl acetate (3×100 ml). The combined organic layers were washed with sodium hydroxide solution (1M, 100 ml) and water (100 ml), dried over sodium sulfate and concentrated. The crude product was purified by column chromatography on silica gel (ethyl acetate/n-heptane 1:1) to yield 5.2 g (78%) N-(1-ethyl-3,3-dimethyl-5-nitro-2-oxo-2,3-dihydro-1H-indol-6-yl)-acetamide as a yellow solid.

MS: M=292.0 (API+)

$^1$H-NMR (400 MHz. DMSO): δ (ppm)=1.16 (t, 3H), 1.31 (s, 6H), 2.13 (s, 3H), 3.71 (m, 2H), 7.54 (s, 1H), 8.12 (s, 1H), 10.39 (br, 1H)

6-Amino-1-ethyl-3,3-dimethyl-5-nitro-1,3-dihydro-indol-2-one

N-(1-ethyl-3,3-dimethyl-5-nitro-2-oxo-2,3-dihydro-1H-indol-6-yl)-acetamide (5.2 g, 17.85 mmol) was dissolved in ethanol (40 ml). After addition of hydrochloric acid (25%, 8 ml, 81.44 mmol) the mixture was stirred under reflux for 3 h. The reaction mixture was allowed to cool down to room temperature and then quenched with water (80 ml). The yellow precipitate was isolated by suction and washed with ethanol/water (1:1). The solid was dissolved in ethyl acetate, dried over sodium sulfate and concentrated to yield 4.15 g (93%) 6-amino-1-ethyl-3,3-dimethyl-5-nitro-1,3-dihydro-indol-2-one as a orange solid.

MS: M=250.0 (API+)

$^1$H-NMR (400 MHz, DMSO): δ (ppm)=1.15 (t, 3H), 1.27 (s, 6H), 3.64 (m, 2H), 6.54 (s, 1H), 7.67 (br, 2H), 7.95 (s, 1H)

5,6-Diamino-1-ethyl-3,3-dimethyl-1,3-dihydro-indol-2-one

To a solution of 6-amino-1-ethyl-3,3-dimethyl-5-nitro-1,3-dihydro-indol-2-one (4.15 g, 16.65 mmol) in ethanol (80 ml) PtO$_2$ (0.4 g) was added and the mixture hydrogenated at room temperature for 3.5 h. After filtration and evaporation of the solvents 3.25 g (89%) 5,6-diamino-1-ethyl-3,3-dimethyl-1,3-dihydro-indol-2-one was isolated as orange solid.

MS: M=220.0 (API+)

$^1$H-NMR (400 MHz, DMSO): δ (ppm)=1.10 (t, 3H), 1.13 (s, 6H), 3.53 (m, 2H), 4.08 (br, 2H), 4.48 (br, 2H), 6.27 (s, 1H), 6.50 (s, 1H)

Preparation of 5,6-diamino-1,3,3-trimethyl-1,3-dihydro-indol-2-one 5,6-diamino-1,3,3-trimethyl-1,3-dihydro-indol-2-one was prepared in an analogous 6-step-synthesis as described for 5,6-diamino-1-ethyl-3,3-dimethyl-1,3-dihydro-indol-2-one.

MS: M=206.1 (API+)

$^1$H-NMR (400 MHz. DMSO): δ (ppm)=1.57 (s, 6H), 3.43 (s, 3H), 4.94 (br, 4H), 6.66 (s, 1H), 6.95 (s, 1H)

Preparation of 5,6-diamino-3,3-dimethyl-1-propyl-1,3-dihydro-indol-2-one 5,6-diamino-3,3-dimethyl-1-propyl-1,3-dihydro-indol-2-one was prepared in an analogous 6-step-synthesis as described for 5,6-diamino-1-ethyl-3,3-dimethyl-1,3-dihydro-indol-2-one.

MS: M=234.1 (API+)

$^1$H-NMR (400 MHz, DMSO): δ (ppm)=0.82 (t, 3H), 1.15 (s, 6H), 1.58 (m, 2H), 3.46 (q, 2H), 4.16 (br, 2H), 4.45 (br, 2H), 6.27 (s, 1H), 6.50 (s, 1H)

Preparation of 5,6-diamino-1-isopropyl-3,3-dimethyl-1,3-dihydro-indol-2-one 5,6-diamino-3,3-dimethyl-1-isopropyl-1,3-dihydro-indol-2-one was prepared in an analogous 6-step-synthesis as described for 5,6-diamino-1-ethyl-3,3-dimethyl-1,3-dihydro-indol-2-one.

MS: M=234.1 (API+)

$^1$H-NMR (400 MHz, DMSO): δ (ppm)=1.12 (s, 6H), 1.33 (d, 6H), 4.09 (br, 2H), 4.40 (m, 1H), 4.46 (br, 2H), 6.46 (s, 1H), 6.48 (s, 1H)

Preparation of 5-trifluoromethyl-2H-pyrazole-3-carboxylic acid

1-Benzyl-5-furan-2-yl-3-trifluoromethyl-1H-pyrazole

To a solution of 50 g (0.240 mol) 4,4,4-trifluoro-1-(2-furyl)-1,3-butanedione in 24 ml (0.024 mol) 1M solution of hydrogen chloride in ethanol and further 520 ml EtOH was added. 50 g (0.248 mol) benzylhydrazine dihydrochloride in small portion at room temperature. The reaction mixture was then heated under reflux for 7 h. After cooling to room temperature the reaction mixture was neutralized with saturated NaHCO$_3$, the EtOH was distilled off and the residual oil/water mixture was extracted with 300 ml dichloromethane. The organic phase was washed twice with 100 ml water and dried over Na$_2$SO$_4$ and concentrated in vacuo to give 73.7 g 1-benzyl-5-furan-2-yl-3-trifluoromethyl-1H-pyrazole as a brown oil which was used crude for the next reaction.

MS: M=293.0 (API+)

2-Benzyl-5-trifluoromethyl-2H-pyrazole-3-carboxylic acid

To a solution of 9.5 g (0.0325 mol) 1-benzyl-5-furan-2-yl-3-trifluoromethyl-1H-pyrazole in 350 mL acetone was added 27.2 g (0.172 mol) potassium permanganate in 450 ml water. The reaction mixture was heated at 60° C. for 4 h. After cooling to room temperature 200 ml 2-propanol were added and the mixture was stirred over night, it was filtered through a Celite pad and washed with 1 l acetone. The filtrate was concentrated in vacuo down to 150 mL. The residue was dissolved in 20 mL 2M NaOH and 150 mL water. The resulting aqueous phase was washed twice with 70 ml ethyl ether and was then acidified with 30 ml 5M HCl solution. The suspension was extracted with 200 and 50 ml ethyl acetate (EtOAc). The combined organic extracts were washed with 30 mL water and 5 mL brine and concentrated. The residue was purified by silica gel chromatography (CH$_2$Cl$_2$ with 1% acetic acid) to give 6.1 g (0.022 mol, 67%) of 2-benzyl-5-trifluoromethyl-2H-pyrazole-3-carboxylic acid as a off-white solid. MS: M=271.1 (ESI+)

5-Trifluoromethyl-2H-pyrazole-3-carboxylic acid

About 50 ml ammonia were condensed into a three-neck-flask in an ethanol-dry ice bath and 100 mg (3.70 mmol) 2-benzyl-5-trifluoromethyl-2H-pyrazole-3-carboxylic acid were added. To the solution sodium was added in small portions until the blue color stayed for more then 5 minutes (about 260 mg, 11.3 mmol). The ammonia was evaporated overnight. Water was added and acidified with 2N HCl solution. The aqueous phase was extracted twice with ethyl acetate, the combined organic phases were dried over $Na_2SO_4$, the solvent was evaporated in vacuo to give 560 mg (3.11 mmol, 84%) 5-trifluoromethyl-2H-pyrazole-3-carboxylic acid as a yellow solid that was used without further purification. MS: M=179.0 (API−)

5-Methoxy-1H-pyrazole-3-carboxylic acid ethyl ester

5-Hydroxy-1H-pyrazole-3-carboxylic acid ethyl ester (300 mg, 1.92 mmol) was dissolved in anhydrous N,N-dimethylformamide (DMF) (35 ml) and cesium carbonate (626 mg, 1.92 mmol) was added. The resulting suspension was treated with iodomethane (120 μl, 273 mg, 1.92 mmol) and stirred for 12 h at room temperature. The reaction mixture was quenched with saturated potassium hydrogen sulfate solution and extracted with ethyl acetate (3×100 ml). The combined organic layers were washed with water (50 ml) and brine (50 ml). The extract was dried over sodium sulfate, evaporated and the crude product was purified by column chromatography on silica gel. Elution with ethyl acetate/n-heptane (1:3) yielded 124 mg (38%) of a white solid.

MS: M=171.2 (ESI+)
$^1$H-NMR (400 MHz, DMSO): δ (ppm)=1.29 (t, 3H), 3.79 (s, 3H), 4.29 (q, 2H), 6.21 (s, 1H), 13.10 (br, 1H)

5-Methoxy-1H-pyrazole-3-carboxylic acid

5-Methoxy-1H-pyrazole-3-carboxylic acid ethyl ester (120 mg, 0.71 mmol) was dissolved in tetrahydrofuran (THF) (2 mL). After addition of sodium hydroxide (2M in water; 1 mL) the mixture was stirred under reflux for 2 h. The reaction mixture was cooled to room temperature and acidified (pH 3) by addition of hydrochloric acid and extracted with ethyl acetate (3×20 ml). The extract was dried over sodium sulfate and evaporated to yield 86 mg (86%) of a white solid.

Preparation of 2-(3,3-Bis-methylsulfanyl-acryloyl)-5-ethyl-7,7-dimethyl-5,7-dihydro-1H-imidazo[4,5-f]indol-6-one 5-Ethyl-2-(1-hydroxy-ethyl)-7,7-dimethyl-5,7-dihydro-1H-imidazo[4,5-f]indol-6-one A mixture of 5,6-diamino-1-ethyl-3,3-dimethyl-1,3-dihydro-indol-2-one (10 g, 46 mmol), 2-hydroxy-propionic acid (9.13 g, 91.2 mmol) in HCl (100 mL, 4N) was refluxed for 16 h. After cooling, neutralization with aqueous ammonia (25%) and stirring for 1.5 h the precipitate was filtered and dried in vacuo at 50° C. yielding 12.29 g (95%) of a grey solid.

MS: M=274.3 (ESI+)
$^1$H-NMR (400 MHz, DMSO): δ (ppm)=1.17 (t, 3H), 1.28 (s, 6H), 1.48 (d, 3H), 3.73 (q, 2H), 4.90 (m, 1H), 5.68 (d, 1H, OH), 7.05 (s, 1H), 7.43 (s, 1H), 12.2 (br, 1H)

2-Acetyl-5-ethyl-7,7-dimethyl-5,7-dihydro-1H-imidazo[4,5-f]indol-6-one

5-Ethyl-2-(1-hydroxy-ethyl)-7,7-dimethyl-5,7-dihydro-1H-imidazo[4,5-f]indol-6-one (13 g, 47.6 mmol) and manganese(IV)dioxide (16.54 g, 190 mmol) were suspended in chloroform (400 mL) and stirred at 65° C. for 16 h. The mixture was cooled, filtered over Celite and the filtrate concentrated in vacuo yielding 11.6 g (90%) of a beige solid.

MS: M=272.0 (ESI+)
$^1$H-NMR (400 MHz, DMSO): d (ppm)=1.18 (t, 3H), 1.32 (s, 6H), 2.66 (s, 3H), 3.77 (q, 2H), 7.00 and 7.40 (s, 1H, two tautomeric forms), 7.50 and 7.80 (s, 1H, two tautomeric forms), 13.3 (br, 1H)

2-Acetyl-5-ethyl-7,7-dimethyl-1-(tetrahydro-pyran-2-yl)-5,7-dihydro-1H-imidazo[4,5-f]indol-6-one 2-Acetyl-5-ethyl-7,7-dimethyl-5,7-dihydro-1H-imidazo[4,5-f]indol-6-one (11.7 g, 43.1 mmol) and p-toluenesulfonic acid monohydrate (0.82 g, 4.3 mmol) were dissolved in dichloromethane (200 mL). To this solution 3,4-dihydro-2H-pyrane (4.81 g, 56 mmol) was added and the mixture stirred at reflux for 24 h. The mixture was filtered, the filtrate washed with water (2×100 mL), dried over sodium sulfate and concentrated in vacuo. The crude product was purified by column chromatography on silica (dichloromethane/methanol 93:3) yielding 6.8 g (44%) of a light yellow solid.

MS: M=356.3 (ESI+)
$^1$H-NMR (400 MHz, DMSO): d (ppm)=1.21 (t, 3H), 1.32 (s, 6H), 1.59-2.23 (m, 6H), 2.70 (s, 3H), 3.65 (t, 1H), 3.80 (m, 2H), 4.15 (d, 1H), 6.47 (d, 1H), 7.30 (s, 1H), 7.82 (s, 1H)

2-(3,3-Bis-methylsulfanyl-acryloyl)-5-ethyl-7,7-dimethyl-1-(tetrahydro-pyran-2-yl)-5,7-dihydro-1H-imidazo[4,5-f]indol-6-one To a suspension of sodium hydride (0.57 g, 22.5 mmol) in toluene (20 mL) at 80° C. tert-butanol (0.88 g, 11.8 mmol) was added and the mixture stirred for 2 h. After cooling to room temperature a suspension of 2-acetyl-5-ethyl-7,7-dimethyl-1-(tetrahydro-pyran-2-yl)-5,7-dihydro-1H-imidazo[4,5-f]indol-6-one (2 g, 5.63 mmol) and carbon disulfide (0.43 g, 5.63 mmol) in N,N-dimethylformamide (DMF) (12 mL) was added in small portions, the mixture stirred for 30 min at room temperature and finally stirred for 30 min at 80° C. After cooling to room temperature, water (20 mL) and ethyl acetate (15 mL) were added, the layers separated and the aqueous layer extracted with ethyl acetate (3×10 mL). The combined organic phases were washed with water (3×10 mL) and concentrated in vacuo to yield 2.27 g (88%) of 2-(3,3-bis-methylsulfanyl-acryloyl)-5-ethyl-7,7-dimethyl-1-(tetrahydro-pyran-2-yl)-5,7-dihydro-1H-imidazo[4,5-f]indol-6-one which was partially deprotected in the course of the reaction. It was used without any further purification in the next step.

MS: M=460.1 (ESI+)

2-(3,3-Bis-methylsulfanyl-acryloyl)-5-ethyl-7,7-dimethyl-5,7-dihydro-1H-imidazo[4,5-f]indol-6-one Crude 2-(3,3-bis-methylsulfanyl-acryloyl)-5-ethyl-7,7-dimethyl-1-(tetrahydro-pyran-2-yl)-5,7-dihydro-1H-imidazo[4,5-f]indol-6-one (2.25 g, 4.9 mmol) and p-toluenesulfonic acid monohydrate (0.5 g, 2.6 mmol) was dissolved in methanol (25 mL) and water (3 mL) and stirred at reflux for 3 h. After cooling to room temperature, water (50 mL) was added and the mixture extracted with etyhl acetate (3×50 mL). The combined organic layers were washed with water and concentrated in vacuo. The crude product was recrystallized from methanol to yield 2-(3,3-bis-methylsulfanyl-acryloyl)-5-ethyl-7,7-dimethyl-5,7-dihydro-1H-imidazo[4,5-f]indol-6-one (0.71 g, 39%) as yellow solid.

MS: M=376.3 (ESI+)
$^1$H-NMR (400 MHz, CDCl3): d (ppm)=1.31 (t, 3H), 1.42 (s, 6H), 2.63 (s, 3H), 2.72 (s, 3H), 3.83 (m, 2H), 7.13 and 7.25 (s, 1H, two tautomeric forms), 7.49 (s, 1H), 7.58 and 7.65 (s, 1H, two tautomeric forms), 11.5 (br, 1H)

B: Final Products

Examples 1 to 43

Standard Procedure

Preparation of 1-Isopropyl-6-(5-methyl-1H-pyrazol-3-yl)-3,5-dihydro-1H-benzo[1,2-d;4,5-d']diimidazol-2-one (Example 11)

5-Methyl-1H-pyrazole-3-carboxylic acid (126 mg, 1 mmol) and 5,6-diamino-1-isopropyl-1,3-dihydro-benzoimidazol-2-one (206 mg, 1 mmol) were heated to 160° C. in a mixture of polyphosphoric acid (5 g) and phosphorus pentoxide (500 mg, 3.5 mmol) for 6 h. This mixture was poured on water (20 ml) and stirring continued until a precipitate formed. After filtration the crude product was suspended in water and neutralized by the addition of aqueous ammonia (25%). The precipitate was collected, washed with water and dried in vacuo. Purification was achieved by chromatography on silica (dichloromethane/methanol 95:5) yielding 1-isopropyl-6-(5-methyl-1H-pyrazol-3-yl)-3,5-dihydro-1H-benzo[1,2-d;4,5-d']diimidazol-2-one as slightly yellow solid. Yield 36 mg (12%)

Using the experimental conditions reported above and the appropriate starting materials, the following derivatives 1 to 43 were prepared:

| Example No. | Systematic Name | MS (Method) | $^1$H-NMR |
|---|---|---|---|
| 1 | 7,7-Dimethyl-2-(5-methyl-2H-pyrazol-3-yl)-3,5,6,7-tetrahydro-imidazo[4,5-f]indole | 268.3 (ESI+) | |
| 2 | 1-[7,7-Dimethyl-2-(5-methyl-2H-pyrazol-3-yl)-6,7-dihydro-3H-imidazo[4,5-f]indol-5-yl]-ethanone | 310.3 (ESI+) | |
| 3 | 8,8-Dimethyl-2-(5-methyl-1H-pyrazol-3-yl)-1,5,7,8-tetrahydro-imidazo[4,5-g]quinolin-6-one | 296.3 (ESI+) | |
| 4 | 2-(5-Isobutyl-2H-pyrazol-3-yl)-8,8-dimethyl-1,5,7,8-tetrahydro-imidazo[4,5-g]quinolin-6-one | 338.0 (API+) | |
| 5 | 7,7-Dimethyl-2-(5-methyl-2H-pyrazol-3-yl)-5,7-dihydro-3H-imidazo[4,5-f]indol-6-one | 282.2 (ESI+) | [D6]DMSO, 400 MHz: 1.30(d, 6H), 2.32(s, 3H), 6.54 and 6.56(s, 1H, two tautomeric forms), 6.89 and 7.00(s, 1H, two tautomeric forms), 7.30 and 7.48(s, 1H, two tautomeric forms), 10.18 and 10.23(br, 1H, two tautomeric forms), 12.39 and 12.53 (br, 1H, two tautomeric forms), 12.85 and 12.89 (br, 1H, two tautomeric forms) |
| 6 | 2-(5-isobutyl-2H-pyrazol-3-yl)-7,7-dimethyl-5,7-dihydro-1H-imidazo[4,5-f]indol-6-one | 324.0 (API+) | |

-continued

| Example No. | Systematic Name | MS (Method) | ¹H-NMR |
|---|---|---|---|
| 7 | 2-(5-Methyl-2H-pyrazol-3-yl)-spiro[7,7-cyclopentan-5,7-dihydro-3H-imidazo[4,5-f]indol-6]-one; or according to the actual IUPAC-nomenclature: 2-(5-Methyl-2H-pyrazol-3-yl)-spiro-5,7-dihydro[cyclopentane-1',7-imidazo[4,5-f]indol]-6(3H)-one | 308.3 (ESI+) | |
| 8 | 2-(5-Isobutyl-2H-pyrazol-3-yl)-spiro[7,7-cyclopentan-5,7-dihydro-1H-imidazo[4,5-f]indol-6]-one; or according to the actual IUPAC-nomenclature: 2-(5-Isobutyl-2H-pyrazol-3-yl)-spiro-5,7-dihydro[cyclopentane-1',7-imidazo[4,5-f]indol]-6(3H)-one | 350.1 (API+) | |
| 9 | 6-(5-Methyl-1H-pyrazol-3-yl)-3,5-dihydro-1H-benzo[1,2-d;4,5-d']diimidazol-2-one | 255 (API+) | [D6]DMSO, 400 MHz: 2.30(s, 3H), 6.53(s, 1H), 7.00 (s, 2H), 10.42(br, 2H), 12.38(br, 1H), 12.86(br, 1H) |
| 10 | 3-Methyl-6-(5-methyl-1H-pyrazol-3-yl)-3,5-dihydro-1H-benzo[1,2-d;4,5-d']diimidazol-2-one | 269.1 (API+) | [D6]DMSO, 400 MHz: 2.30(s, 3H), 3.36(s, 3H), 6.54 (s, 1H), 7.05(s, 1H), 7.13(s, 1H), 10.65(br, 1H), 12.50(br, 1H), 12.86(br, 1H) |
| 11 | 3-Isopropyl-6-(5-methyl-1H-pyrazol-3-yl)-3,5-dihydro-1H-benzo[1,2-d;4,5-d']diimidazol-2-one | 297.2 (API+) | [D6]DMSO, 400 MHz: 1.47(d, 6H), 2.31(s, 3H), 4.61 (m, 1H), 6.53(s, 1H), 6.98(s, 1H), 7.12(d, 1H), 7.39 (s, 1H), 10.61(br, 1H) |
| 12 | 5-Ethyl-7,7-dimethyl-2-(5-methyl-1H-pyrazol-3-yl)-5,7-dihydro-3H-imidazo[4,5-f]indol-6-one | 310.1 (API+) | [D6]DMSO, 400 MHz: 1.17(t, 3H), 1.31(d, 6H), 2.31 (s, 3H), 3.75(q, 2H), 6.58(s, 1H), 6.95 and 7.22(s, 1H, two tautomeric forms), 7.39 and 7.55(s, 1H, two tautomeric forms), 12.60(br, 1H), 12.90(br, 1H) |
| 13 | 5-Ethyl-7,7-dimethyl-2-(5-propyl-2H-pyrazol-3-yl)-5,7-dihydro-3H-imidazo[4,5-f]indol-6-one | 338.1 (API+) | [D6]DMSO, 400 MHz: d=12.64 (bs, 1H), 7.48(s, 1H), 7.09(s, 1H), 6.59(s, 1H), 3.76 (q, 2H), 2.64(t, 2H), 1.72-1.63(m, |

-continued

| Example No. | Systematic Name | MS (Method) | ¹H-NMR |
|---|---|---|---|
| | | | 2H), 1.31(s, 6H), 1.19(t, 3H), 0.95(t, 3H) |
| 14 | 5,7,7-Trimethyl-2-(5-propyl-2H-pyrazol-3-yl)-5,7-dihydro-3H-imidazo[4,5-f]indol-6-one | 324.1 (API+) | |
| 15 | 5-Ethyl-2-(5-isobutyl-2H-pyrazol-3-yl)-7,7-dimethyl-5,7-dihydro-3H-imidazo[4,5-f]indol-6-one | 352.1 (API+) | |
| 16 | 2-(5-Isobutyl-2H-pyrazol-3-yl)-5,7,7-trimethyl-5,7-dihydro-3H-imidazo[4,5-f]indol-6-one | 338.1 (API+) | |
| 17 | 2-(4,5-Dimethyl-1H-pyrazol-3-yl)-7,7-dimethyl-5,7-dihydro-1H-imidazo[4,5-f]indol-6-one | 294.0 (API−) | |
| 18 | 7,7-Dimethyl-2-[5-(3-methyl-butyl)-1H-pyrazol-3-yl]-5,7-dihydro-1H-imidazo[4,5-f]indol-6-one | 336.1 (API−) | |
| 19 | 2-(5-Ethyl-4-methyl-1H-pyrazol-3-yl)-7,7-dimethyl-5,7-dihydro-1H-imidazo[4,5-f]indol-6-one | 308.1 (API−) | |
| 20 | 7,7-Dimethyl-2-(1H-pyrazol-3-yl)-5,7-dihydro-1H-imidazo[4,5-f]4indol-6-one | 268.0 (ESI+) | |
| 21 | 2-(5-Cyclopropyl-1H-pyrazol-3-yl)-7,7-dimethyl-5,7-dihydro-1H-imidazo[4,5-f]indol-6-one | 308.1 (ESI+) | |
| 22 | 2-(5-Isopropyl-2H-pyrazol-3-yl)-7,7-dimethyl-5,7-dihydro-1H-imidazo[4,5-f]indol-6-one | 310.1 (ESI+) | |
| 23 | 8,8-Dimethyl-2-(5-propyl-2H-pyrazol-3-yl)-1,5,7,8-tetrahydro-imidazo[4,5-g]quinolin-6-one | 324.2 (ESI+) | |
| 24 | 8,8-Dimethyl-2-(1H-pyrazol-3-yl)-1,5,7,8-tetrahydro-imidazo[4,5-g]quinolin-6-one | 282.2 (ESI+) | |
| 25 | 2-(5-Cyclopropyl-1H-pyrazol-3-yl)-8,8-dimethyl-1,5,7,8-tetrahydro-imidazo[4,5-g]quinolin-6-one | 322.2 (ESI+) | |
| 26 | 2-(5-Isopropyl-2H-pyrazol-3-yl)-8,8-dimethyl-1,5,7,8- | 324.2 (ESI+) | |

-continued

| Example No. | | Systematic Name | MS (Method) | ¹H-NMR |
|---|---|---|---|---|
| | | tetrahydro-imidazo[4,5-g]quinolin-6-one | | |
| 27 | [structure] | 2-(2H-pyrazol-3-yl)-spiro-5,7-dihydro[cyclopentane-1',7-imidazo[4,5-f]indol]-6(3H)-one | 294.2 (ESI+) | |
| 28 | [structure] | 2-(5-Isopropyl-2H-pyrazol-3-yl)-spiro-5,7-dihydro[cyclopentane-1',7-imidazo[4,5-f]indol]-6(3H)-one | 336.2 (ESI+) | |
| 29 | [structure] | 2-(5-Propyl-2H-pyrazol-3-yl)-spiro-5,7-dihydro[cyclopentane-1',7-imidazo[4,5-f]indol]-6(3H)-one | 336.2 (ESI+) | |
| 30 | | 5,7,7-Trimethyl-2-(1H-pyrazol-3-yl)-5,7-dihydro-3H-imidazo[4,5-f]indol-6-one | 282.2 (ESI+) | |
| 31 | | 5,7,7-Trimethyl-2-(5-methyl-1H-pyrazol-3-yl)-5,7-dihydro-3H-imidazo[4,5-f]indol-6-one | 296.0 (API+) | [D6]DMSO, 400 MHz: d=12.89(m, 1H), 12.61(m, 1H), 7.56-6.94(m, 2H), 6.55(s, 1H), 3.19 (s, 3H), 2.32(s, 3H), 1.31(s, 6H) |
| 32 | | 5-Ethyl-7,7-dimethyl-2-(1H-pyrazol-3-yl)-5,7-dihydro-3H-imidazo[4,5-f]indol-6-one | 296.2 (ESI+) | |
| 33 | | 5-Ethyl-7,7-dimethyl-2-(5-propyl-2H-pyrazol-3-yl)-5,7-dihydro-3H-imidazo[4,5-f]indol-6-one; compound with acetic acid | 338.2 (ESI+) | |
| 34 | | 5-Isopropyl-7,7-dimethyl-2-(5-methyl-2H-pyrazol-3-yl)-5,7-dihydro-1H-imidazo[4,5-f]indol-6-one | 324.1 (API+) | [D6]DMSO, 400 MHz: 1.28(s, 6H), 1.45(d, 3H), 2.31 (s, 3H), 4.56(br, 1H), 6.55(s, 1H), 6.88 and 7.09 and 7.32 and 7.54(2H, two tautomeric forms), 12.61(NH), 12.87(NH) |
| 35 | | 5-Isopropyl-7,7-dimethyl-2-(5-propyl-2H-pyrazol-3-yl)-5,7-dihydro-1H-imidazo[4,5-f]indol-6-one | 352.2 (API+) | [D6]DMSO, 400 MHz: 0.95(t, 3H), 1.29(s, 6H), 1.44 (d, 6H), 1.66(m, 2H), 2.64(t, 2H), 4.56(br, 1H), 6.57 (s, 1H), 7.71 and 7.31(1H, two |

-continued

| Example No. | Systematic Name | MS (Method) | ¹H-NMR |
|---|---|---|---|
| | | | tautomeric forms), 7.35 and 7.55(1H, two tautomeric forms), 12.49 and 12.60(NH, two tautomeric forms), 12.90(NH) |
| 36 | 7,7-Dimethyl-2-(5-methyl-2H-pyrazol-3-yl)-5-propyl-5,7-dihydro-1H-imidazo[4,5-f]indol-6-one | 324.1 (API+) | [D6]DMSO, 400 MHz: 0.88(t, 3H), 1.31(s, 6H), 1.66 (m, 2H), 2.31(s, 3H), 3.69(t, 2H), 6.55(s, 1H), 6.95 and 7.22(1H, two tautomeric forms), 7.35 and 7.56(1H, two tautomeric forms), 12.54 and 12.62(NH, two tautomeric forms), 12.88(NH) |
| 37 | 7,7-Dimethyl-5-propyl-2-(5-propyl-2H-pyrazol-3-yl)-5,7-dihydro-3H-imidazo[4,5-f]indol-6-one | 352.1 (API+) | [D6]DMSO, 400 MHz: 0.88(t, 3H), 0.95(t, 3H), 1.31 (s, 6H), 1.67(m, 4H), 2.64(t, 2H), 3.69(t, 2H), 6.58 (s, 1H), 6.95 and 7.23(s, 1H, two tautomeric forms), 7.39 and 7.57(s, 1H, two tautomeric forms), 12.60(br, 1H), 12.91(br, 1H) |
| 38 | 7,7-Dimethyl-2-(5-trifluoromethyl-2H-pyrazol-3-yl)-5,7-dihydro-1H-imidazo[4,5-f]indol-6-one | 336.0 (API+) | [D6]DMSO, 400 MHz: 1.32(s, 6H), 6.94 and 7.04(1H, two tautomeric forms), 7.22 and 7.51(1H, two tautomeric forms), 7.28 and 7.60(1H, two tautomeric forms), 10.35(NH), 12.88 and 12.98 (NH, two tautomeric forms), 14.64(NH) |
| 39 | 5-Ethyl-7,7-dimethyl-2-(5-trifluoromethyl-1H-pyrazol-3-yl)-5,7-dihydro-3H-imidazo[4,5-f]indol-6-one | 364.1 (API+) | [D6]DMSO, 400 MHz: 1.18(t, 3H), 1.32(d, 6H), 3.79 (q, 2H), 7.20(s, 1H), 7.28(s, 1H), 7.63(s, 1H), |
| 40 | 5-Isopropyl-7,7-dimethyl-2-(5-trifluoromethyl-2H-pyrazol-3-yl)-5,7-dihydro-1H-imidazo[4,5-f]indol-6-one | 378.0 (API+) | [D6]DMSO, 400 MHz: 1.18(s, 6H), 1.46(d, 6H), 4.58 (m, 1H), 7.23 (br, 1H), 7.28(s, 1H), 7.62(br, 1H), 12.99(NH), 14.67 (NH) |
| 41 | 7,7-Dimethyl-5-propyl-2-(5-trifluoromethyl-2H-pyrazol-3-yl)-5,7-dihydro-1H-imidazo[4,5-f]indol-6-one | 378.0 (API+) | [D6]DMSO, 400 MHz: 0.88(t, 3H), 1.34(s, 6H), 1.67 (m, 2H), 3.74(t, 2H), 7.18(br, 1H), 7.28(s, 1H), 7.63 (br, 1H), 13.02(NH), 14.64(NH) |
| 42 | 5,7,7-Trimethyl-2-(5-trifluoromethyl-2H-pyrazol-3-yl)-5,7-dihydro-3H-imidazo[4,5-f]indol-6-one | 350.0 (API+) | [D6]DMSO, 400 MHz: d=14.66(s, 1H), 13.04(s, 1H), 7.63(m, 1H), 7.29 (m, 1H), 7.15(m, 1H), 3.22(s, 3H), 1.34(s, 6H) |

| Example No. | | Systematic Name | MS (Method) | 1H-NMR |
|---|---|---|---|---|
| 43 | (structure) | 2-(5-Cyclopropyl-2H-pyrazol-3-yl)-spiro-5,7-dihydro[cyclopentane-1',7-imidazo[4,5-f]indol]-6(3H)-one | 334.2 (ESI+) | |

Example 44

5-Ethyl-2-(5-methoxy-1H-pyrazol-3-yl)-7,7-dimethyl-5,7-dihydro-3H-imidazo[4,5-f]indol-6-one 5-Methoxy-1H-pyrazole-3-carboxylic acid (86 mg, 0.61 mmol), 1-hydroxybenzotriazole hydrate (111 mg, 0.73 mmol) and triethylamine (253 µl, 184 mg, 1.82 mmol) were dissolved in N,N-dimethylformamide (DMF) (2 ml) and after the addition of 1-(3-dimethylaminopropyl)-3-ethylcarbodiimide hydrochloride (EDC) (139 mg, 0.73 mmol) dissolved in DMF (2 ml) the reaction mixture was stirred at room temperature. After 1 hour a solution of 5,6-diamino-1-ethyl-3,3-dimethyl-1,3-dihydro-indol-2-one in DMF (2 ml) was added and the reaction mixture was stirred at room temperature for 16 hours. The solvent was removed under reduced pressure, the residue was quenched with water (20 ml) and extracted with ethyl acetate (3×20 mL). The combined organic layers were washed with brine (15 ml), dried over sodium sulfate and evaporated. The residue was dissolved in ethanol (5 ml) and after the addition of hydrochloric acid (10 M, 2 ml) it was stirred under reflux for 2 hours. The ethanol was evaporated and the residue was adjusted to pH 9-10 with ammonium hydroxide. After the addition of water (20 ml) the aqueous phase was extracted with ethyl acetate (3×20 ml). The combined organic layers were washed with brine (10 ml), dried over sodium sulfate and evaporated. The crude product was purified by column chromatography on silica gel. Elution with ethyl acetate/n-heptane (9:1) yielded 56 mg (28%) of an off-white solid.

MS: M=326.1 (API+)

1H-NMR (400 MHz. DMSO): δ (ppm)=1.19 (t, 3H), 1.32 (s, 6H), 3.76 (q, 2H), 3.84 (s, 3H), 6.28 (s, 1H), 7.14 (s, 1H), 7.56 (s, 1H), 12.80 (br, 2H)

Example 45

5-Ethyl-7,7-dimethyl-2-(5-methylsulfanyl-1H-pyrazol-3-yl)-5,7-dihydro-1H-imidazo[4,5-f]indol-6-one Hydrazine monohydrate (0.92 g, 1.8 mmol) was added to a suspension of 2-(3,3-bis-methylsulfanyl-acryloyl)-5-ethyl-7,7-dimethyl-1-(tetrahydro-pyran-2-yl)-5,7-dihydro-1H-imidazo[4,5-f]indol-6-one (0.68 g, 1.81 mmol) in acetonitrile (15 mL) and stirred for 24 h. After cooling to room temperature the precipitate was collected, washed with acetonitrile and ether to yield 0.5 g (81%) of a pale white powder.

MS: M=342.1 (API+)

1H-NMR (400 MHz, DMSO): δ (ppm)=1.19 (t, 3H), 1.31 (s, 6H), 2.53 (s, 3H), 3.76 (m, 2H), 6.83 (s, 1H), 6.95-7.65 (br m, 2H, tautomeric forms), 12.75 (br, 1H), 13.45 (br, 1H)

Pharmacological Activity $IC_{50}$ Determination for Inhibitors of Aurora A (96 MTP-ELISA)

Assay Principle

Aurora A is a serine threonine kinase involved in spindle assembly and chromosome segregation.

The assay is a typically ELISA-type assay where biotinylated substrate (PKB-GSK2) is phosphorylated. Phosphorylation is detected by peroxidase (POD) labelled polyclonal antibody (PAK<M-Ig>S-IgG-POD) and phosphopeptide monoclonal antibody (Mab) (MAK<P-GSK>M-27E5-IgG). The assay is validated for $IC_{50}$-determination.

Materials

Assay plates 96-well polystyrene plates, streptavidin-coated,

Samples 10 mM in dimethylsulfoxide (DMSO)

Aurora A-His-4 C-terminally Histidine$_4$ (His$_4$)-tagged Aurora A full-length protein, stock solution 0.7 mg/ml, final conc.: 250 ng/ml PKB-GSK2 biotinylated peptide derived from human GSK3-alpha sequence (Biotin-SGRARTSSFAEPGG-CONH$_2$), stock solution 600 µM, final conc.: 200 nM PAK<M-Ig>S-IgG-POD Anti-mouse IgG, horse radish peroxidase(HRP)-linked Antibody, diluted in 3% BSA/PBS-T (1:10000), (Cell Signaling, Cat. No.: 7076)

MAK<P-GSK>M-27E5-IgGPhospho-GSK-3-alpha (Ser 21) (27E5) Monoclonal Antibody, stock solution 1,85 mg/ml, diluted in 3% BSA/PBS-T (1:6000), final conc.: 0.31 µg/ml, (Cell Signaling, Cat. No.: 9337B)

ATP Adenosine-5'-triphosphate 1 mM, diluted in kinase buffer, (Roche Diagnostics GmbH, Cat. No.: 127531-001,), final conc.: 4 µM TRIS 2-Amino-2-hydroxymethyl-1,3-propoanediol ("tris-(hydroxymethyl)-aminomethane") (MERCK, Cat. No.: 108382.2500)

BSA Bovine Serum Albumin Fraction V, fatty acid free (Roche Diagnostics GmbH, Cat. No. 9100221)

EDTA Titriplex III (di-Sodium-EDTA di-Hydrate), 120 mM, (MERCK, Cat. No.: 1.08418.1000)

ABTS buffer ABTS (2,2'-azino-bis(3-ethylbenzthiazoline-6-sulfonic acid)) 16.7 mg/ml (Roche Diagnostics GmbH, Cat. No.: 1204530)

ABTS tablets dissolve one ABTS tablet in 50 ml of working solution (ABTS buffer) (Roche Diagnostics GmbH, Cat. No.: 1112422)

Tween 20 Polysorbat 20 (Roche Diagnostics GmbH, Cat. No.: 10006394-001)

DTT 1,4-Dithiothreitol (Roche Diagnostics GmbH, Cat. No.: 197777)

$MgCl_2 \times 6H_2O$ MERCK, Cat. No.: 105833.1000

Kinase buffer 50 mM TRIS, 10 mM $MgCl_2$, 1 mM DTT, 0.1% Tween 20, pH 7.8

PBS-T (=Wash buffer) (PBS-T) 10 g/l PBS (Phosphate buffered saline) with 0.033% Tween 20

3% BSA/PBS-T 3% BSA dissolved in PBS-T

Method

This assay is performed in 96-well format for $IC_{50}$ determination with 5 samples (each with 8 concentrations by twofold testing), 100 μl incubation volume and the following plate layout:

|   | 1 | 2 | 3 | 4 | 5 | 6 | 7 | 8 | 9 | 10 | 11 | 12 |
|---|---|---|---|---|---|---|---|---|---|---|---|---|
| A | NC | RS a | RS a | S1a | S1a | S2a | S2a | NC | S3a | S3a | S4a | S4a |
| B | NC | RS b | RS b | S1b | S1b | S2b | S2b | NC | S3b | S3b | S4b | S4b |
| C | NC | RS c | RS c | S1c | S1c | S2c | S2c | NC | S3c | S3c | S4c | S4c |
| D | NC | RS d | RS d | S1d | S1d | S2d | S2d | NC | S3d | S3d | S4d | S4d |
| E | PC | RS e | RS e | S1e | S1e | S2e | S2e | PC | S3e | S3e | S4e | S4e |
| F | PC | RS f | RS f | S1f | S1f | S2f | S2f | PC | S3f | S4f | S4f | S4f |
| G | PC | RS g | RS g | S1g | S1g | S2g | S2g | PC | S3g | S4g | S4g | S4g |
| H | PC | RS h | RS h | S1h | S1h | S2h | S2h | PC | S3h | S4h | S4h | S4h |

NC negative control, without ATP, 1% DMSO
PC positive control, with ATP, 1% DMSO
S samples, with ATP, 1% DMSO, final conc.: a = 100 μM, b = 20 μM, c = 4 μM, d = 0.8 μM, e = 0.16 μM, f = 0.032 μM, g = 0.0064 μM, h = 0.00128 μM Step/Action 1. Sample preparation: add 24 μl per well samples (descending sequence) diluted in kinase buffer to assay plate (final conc. for DMSO 1%).

2. Add directly 16 μl Aurora-A-his-4 diluted in kinase buffer to assay plate.

3. Add directly 40 μl per well PKB-GSK2/ATP mixture to assay plate, (final conc.: Aurora A=250 ng/ml, GSK2=200 nM, ATP=4 μM). Negative control: without ATP.

4. Incubate assay plate for exactly 90 min at room temperature.

5. Stop reaction by adding 20 μl EDTA in all wells.

6. Wash assay plate 3× with 200 μl washing buffer per well.

7. Add 100 μl MAK<P-GSK>M27E5-IgG (1:10000) and PAK<M-Ig>S-IgG-POD (1:6000) dissolved in 3% BSA/PBS-T to assay plate per well.

8. Incubate assay plate for 60 min at room temperature.

9. Wash assay plate 3× with 200 μl washing buffer per well

10. Add 100 μl ABTS solution to assay plate per well, incubate for approx. 4 min at RT on MTP shaker.

11. Measure absorption at 405/492 nm.

12. Calculate % inhibition as:

$$(1-(E_{sample}-E_{NC})/(E_{PC}-E_{NC})) \times 100$$

13. Calculate $IC_{50}$ using a non-linear curve fit (XLfit software (ID Business Solution Ltd., Guilford, Surrey, UK))

TABLE 1

Results:

| Examples | IC50 Aurora A kinase inhibition [nM] |
|---|---|
| 11 | 158 |
| 3 | 212 |
| 2, 5, 7, 10, 17, 18, 19, 21, 23, 25, 27, 31, 34, 35, 36, 37 | 10-500 |
| 4, 6, 9, 24, 28, 29, 41 | 500-1500 |

Antiproliferative Activity

The activity of the present compounds as antiproliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCI-247) were cultivated in RPMI 1640 medium with GlutaMAX™ I (Invitrogen, Cat-No. 61870-010), 2.5% Fetal Calf Serum (FCS, Sigma Cat.-No. F4135 (FBS)); 100 Units/ml penicillin/100 μg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 μM to 0.0015 μM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:

Medium: RPMI 1640 with GlutaMAX™ I (Invitrogen, Cat-Nr. 61870), 5% FCS (Sigma Cat.-No. F4135), Pen/Strep (Invitrogen, Cat No. 15140).

HCT116 (ATCC-No. CCI-247): 1000 cells in 60 μl per well of 384 well plate (Greiner 781098, μClear-plate white)

After seeding incubate plates 24 h at 37° C., 5% $CO_2$

2nd. Day: Induction (Treatment with Compounds, 10 Concentrations):

In order to achieve a final concentration of 30 μM as highest concentration 3.5 μl of 10 mM compound stock solution were added directly to 163 μl media. Then step e) of the dilution procedure described below, was followed.

In order to achieve the second highest to the lowest concentrations, a serial dilution with dilution steps of 1:3 was followed according to the procedure (a-e) as described here below:
- for the second highest concentration add 10 μl of 10 mM stock solution of compound to 20 μl dimethylsulfoxide (DMSO)
- dilute 8×1:3 (always 10 μl to 20 μl DMSO) in this DMSO dilution row (results in 9 wells with concentrations from 3333.3 μM to 0.51 μM)
- dilute each concentration 1:47.6 (3.5 μl compound dilution to 163 μl media)
- add 10 μl of every concentration to 60 μl media in the cell plate resulting in final concentration of DMSO: 0.3% in every well and resulting in 10 final concentration of compounds ranging from 30 μM to 0.0015 μM.

Each compound is tested in triplicate.
Incubate 120 h (5 days) at 37° C., 5% $CO_2$ Analysis:
Add 30 μl CellTiter-Glo™ Reagent (prepared from Cell-Titer-Glo™ Buffer and CellTiter-Glo™ Substrate (lyophilized) purchased from Promega) per well,
shake 15 minutes at room temperature
incubate further 45 minutes at room temperature without shaking Measurement:
Victor 2 scanning multiwell spectrophotometer (Wallac), Luminescence mode (0.5 sec/read, 477 nm)
Determine IC50 using a non-linear curve fit (XLfit software (ID Business Solution Ltd., Guilford, Surrey, UK))
With all compounds a significant inhibition of HCT 116 cell viability was detected, which is exemplified by the compounds shown in Table 1.

TABLE 2

Results:

| Examples | IC50 HCT 116 [μM] |
| --- | --- |
| 42 | 0.98 |
| 14 | 1.20 |
| 2 | 4.67 |
| 4 | 7.65 |
| 5, 6, 7, 8, 12, 13, 15, 16, 17, 18, 20, 22, 23, 24, 27, 28, 30, 31, 32, 33, 34, 35, 36, 37, 39, 41, 43, 44, 45 | 0.1-10.0 |
| 3, 9, 11, 38 | 10.0-100 |

LIST OF REFERENCES

Adams, R. R. et al., Trends Cell Biol. 11 (2001) 49-54

Bastin, R. J., et al., Organic Proc. Res. Dev. 4 (2000) 427-435

Bischoff, J. R., and Plowman, G. D., Trends Cell Biol. 9 (1999) 454-459

DE 34 17 643

DE 36 42 315

DE 37 01 277

Djuric, S. W., et al., J. Med. Chem. 43 (2000) 2975-2981

EP 0 189 103

EP 0 318 902

EP 0 868 519

EP 1 051 500

Giet, R., and Prigent, C., J. Cell Sci. 112 (1999) 3591-3601

Harrington, E. A., et al., Nat. Med. 10 (2004) 262-267

Hunter, T., Cell 50 (1987) 823-829

Isola, J. J., et al., Am. J. Pathology 147 (1995) 905-911

Jia, Z. J., et al., Bioorg. Med. Chem. Lett. 12 (2002) 1651-1655

Mahata, P. K., et al., Tetrahedron 59 (2003) 2631-2639

Martins, M. A. P., et al., Synthesis 15 (2003) 2353-2357

Mertens; A., et al., J. Med. Chem. 30 (1987) 1279-1287

Nigg, E. A., Nat. Rev. Mol. Cell Biol. 2 (2001) 21-32

Ochi, H., et al., Chem. Pharm. Bull. 31 (1983) 1228-1234

Pruitt, J. R., et al., J. Med. Chem. 46 (2003) 5298-5315

Sen, S., et al., J. Natl. Cancer Inst. 94 (2002) 1320-1329

Sewald, N., et al., Liebigs Ann. Chem. (1992) 947-952

Stahl, P. H., and Wermuth, G., (editors), Handbook of Pharmaceutical Salts, Verlag Helvetica Chimica Acta (VHCA), Zürich (2002)

Stanovnik, B., and Svete, J., Science of Synthesis 12 (2002) 15-225

Subramanyam, C., Synth. Commun. 25 (1995) 761-774

U.S. Pat. No. 4,835,280A

U.S. Pat. No. 4,954,498

U.S. Pat. No. 5,212,186A

U.S. Pat. No. 6,207,401 van Herk, T., et al., J. Med. Chem. 46 (2003) 3945-3951 von der Saal, W., et al., J. Med. Chem. 32 (1989) 1481-1491

WO 00/44728

WO 00/47212

WO 01/21594

WO 01/21595

WO 01/21596

WO 01/21597

WO 01/55116

WO 01/77085

WO 02/057259

WO 02/059111

WO 02/059112

WO 02/062789

WO 02/066461

WO 02/068415

WO 02/22601
WO 02/22602
WO 02/22603
WO 02/22604
WO 02/22605
WO 02/22606
WO 02/22607
WO 02/22608
WO 02/50065
WO 02/50066
WO 02/96905
WO 03/035065
WO 03/077921
WO 03/078423
WO 03/078426
WO 03/078427
WO 04/000833
WO 04/005283
WO 04/032928
WO 95/19169
WO 95/23141
WO 97/42187
WO 99/06396

What is claimed:
1. A compound of formula I,

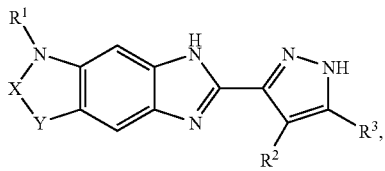

formula I wherein
$R^1$ is alkyl or —C(O)-alkyl;
$R^2$ is hydrogen, alkyl, cyano or halogen;
$R^3$ is hydrogen, alkyl, $(C_3-C_6)$-cycloalkyl, alkoxy or alkylsulfanyl;
X is —C(O)— or —CH$_2$—;
Y is —NH—, —CH$_2$—CR$^4$R$^5$—, —CR$^4$R$^5$—CH$_2$— or —CR$^4$R$^5$—; wherein
$R^4$ is hydrogen or alkyl; and
$R^5$ is hydrogen or alkyl,
or alternatively
$R^4$ and $R^5$ form together with the carbon atom to which they are attached a cycloalkyl ring;
and all pharmaceutically acceptable salts thereof.

2. The compound of claim 1, wherein
$R^1$ is alkyl;
$R^2$ is hydrogen or alkyl;
X is —C(O)—; and
Y is —CR$^4$R$^5$—.

3. The compound of claim 1, wherein
$R^1$ is alkyl;
$R^2$ is hydrogen or alkyl;
$R^3$ is hydrogen, alkyl or $(C_3-C_6)$-cycloalkyl;
X is —C(O)—; and
Y is —CR$^4$R$^5$—.

4. The compound of claim 1, wherein
$R^1$ is alkyl;
$R^2$ is hydrogen or alkyl;
$R^3$ is alkyl which is substituted one or several times by halogen;
X is —C(O)—; and
Y is —CR$^4$R$^5$—.

5. The compound of claim 1 wherein
$R^1$ is alkyl;
$R^2$ is hydrogen or alkyl;
$R^3$ is alkoxy or alkylsulfanyl;
X is —C(O)—; and
Y is —CR$^4$R$^5$—.

6. A compound of claim 1 selected from the group consisting of
7,7-Dimethyl-2-(5-methyl-2H-pyrazol-3-yl)-3,5,6,7-tetrahydro-imidazo[4,5-f]indole;
1-[7,7-Dimethyl-2-(5-methyl-2H-pyrazol-3-yl)-6,7-dihydro-3H-imidazo[4,5-f]indol-5-yl]-ethanone;
8,8-Dimethyl-2-(5-methyl-1H-pyrazol-3-yl)-1,5,7,8-tetrahydro-imidazo[4,5-g]quinolin-6-one;
2-(5-Isobutyl-2H-pyrazol-3-yl)-8,8-dimethyl-1,5,7,8-tetrahydro-imidazo[4,5-g]quinolin-6-one;
7,7-Dimethyl-2-(5-methyl-2H-pyrazol-3-yl)-5,7-dihydro-1H-imidazo[4,5-f]indol-6-one;
2-(5-Isobutyl-2H-pyrazol-3-yl)-7,7-dimethyl-5,7-dihydro-1H-imidazo[4,5-f]indol-6-one;
2-(5-methyl-2H-pyrazol-3-yl)-spiro[7,7-cyclopentan-5,7-dihydro-3H-imidazo[4,5-f]indol]-6-one;
2-(5-Isobutyl-2H-pyrazol-3-yl)-spiro[7,7-cyclopentan-5,7-dihydro-1H-imidazo[4,5-f]indol]-6-one;
6-(5-Methyl-1H-pyrazol-3-yl)-3,5-dihydro-1H-benzo[1,2-d;4,5-d']diimidazol-2-one;
7,7-Dimethyl-2-(5-trifluoromethyl-2H-pyrazol-3-yl)-5,7-dihydro-1H-imidazo[4,5-f]indol-6-one and
2-(5-Cyclopropyl-2H-pyrazol-3-yl)-spiro-5,7-dihydro[cyclopentane-1',7-imidazo[4,5-f]indol]-6(3H)-one.

7. A compound of claim 1 selected from the group consisting of
2-(4,5-Dimethyl-1H-pyrazol-3-yl)-7,7-dimethyl-5,7-dihydro-1H-imidazo[4,5-f]indol-6-one;
7,7-Dimethyl-2-[5-(3-methyl-butyl)-1H-pyrazol-3-yl]-5,7-dihydro-1H-imidazo[4,5-f]indol-6-one;
2-(5-Ethyl-4-methyl-1H-pyrazol-3-yl)-7,7-dimethyl-5,7-dihydro-1H-imidazo[4,5-f]indol-6-one;
7,7-Dimethyl-2-(1H-pyrazol-3-yl)-5,7-dihydro-1H-imidazo[4,5-f]indol-6-one;
2-(5-Cyclopropyl-1H-pyrazol-3-yl)-7,7-dimethyl-5,7-dihydro-1H-imidazo[4,5-f]indol-6-one;
2-(5-Isopropyl-2H-pyrazol-3-yl)-7,7-dimethyl-5,7-dihydro-1H-imidazo[4,5-f]indol-6-one;
8,8-Dimethyl-2-(5-propyl-2H-pyrazol-3-yl)-1,5,7,8-tetrahydro-imidazo[4,5-g]quinolin-6-one;
8,8-Dimethyl-2-(1H-pyrazol-3-yl)-1,5,7,8-tetrahydro-imidazo[4,5-g]quinolin-6-one;
2-(5-Cyclopropyl-1H-pyrazol-3-yl)-8,8-dimethyl-1,5,7,8-tetrahydro-imidazo[4,5-g]quinolin-6-one;
2-(5-Isopropyl-2H-pyrazol-3-yl)-8,8-dimethyl-1,5,7,8-tetrahydro-imidazo[4,5-g]quinolin-6-one;
2-(2H-pyrazol-3-yl)-spiro-5,7-dihydro[cyclopentane-1',7-imidazol[4,5-f]indol]-6(3H)-one;

2-(5-Isopropyl-2H-pyrazol-3-yl)-spiro-5,7-dihydro[cyclopentane-1',7-imidazo[4,5-f]indol]-6(3H)-one and
2-(5-Propyl-2H-pyrazol-3-yl)-spiro-5,7-dihydro[cyclopentane-1',7-imidazo[4,5-f]indol]-6(3H)-one.

8. A compound of claim 1 selected from the group consisting of
5-Ethyl-7,7-dimethyl-2-(5-propyl-2H-pyrazol-3-yl)-5,7-dihydro-3H-imidazo[4,5-f]indol-6-one;
5,7,7-Trimethyl-2-(5-propyl-2H-pyrazol-3-yl)-5,7-dihydro-3H-imidazo[4,5-f]indol-6-one;
5-Ethyl-2-(5-isobutyl-2H-pyrazol-3-yl)-7,7-dimethyl-5,7-dihydro-3H-imidazo[4,5-f]indol-6-one;
2-(5-Isobutyl-2H-pyrazol-3-yl)-5,7,7-trimethyl-5,7-dihydro-3H-imidazo[4,5-f]indol-6-one;
5,7,7-Trimethyl-2-(1H-pyrazol-3-yl)-5,7-dihydro-3H-imidazo[4,5-f]indol-6-one;
5,7,7-Trimethyl-2-(5-methyl-1H-pyrazol-3-yl)-5,7-dihydro-3H-imidazo[4,5-f]indol-6-one;
5-Ethyl-7,7-dimethyl-2-(1H-pyrazol-3-yl)-5,7-dihydro-3H-imidazo[4,5-f]indol-6-one;
5-Ethyl-7,7-dimethyl-2-(5-propyl-2H-pyrazol-3-yl)-5,7-dihydro-3H-imidazo[4,5-f]indol-6-one;
5-Isopropyl-7,7-dimethyl-2-(5-methyl-2H-pyrazol-3-yl)-5,7-dihydro-1H-imidazo[4,5-f]indol-6-one;
5-Isopropyl-7,7-dimethyl-2-(5-propyl-2H-pyrazol-3-yl)-5,7-dihydro-1H-imidazo[4,5-f]indol-6-one;
7,7-Dimethyl-2-(5-methyl-2H-pyrazol-3-yl)-5-propyl-5,7-dihydro-1H-imidazo[4,5-f]indol-6-one;
7,7-Dimethyl-5-propyl-2-(5-propyl-2H-pyrazol-3-yl)-5,7-dihydro-3H-imidazo[4,5-f]indol-6-one;
5-Ethyl-7,7-dimethyl-2-(5-trifluoromethyl-1H-pyrazol-3-yl)-5,7-dihydro-3H-imidazo[4,5-f]indol-6-one;
5-Isopropyl-7,7-dimethyl-2-(5-trifluoromethyl-2H-pyrazol-3-yl)-5,7-dihydro-1H-imidazo[4,5-f]indol-6-one;
7,7-Dimethyl-5-propyl-2-(5-trifluoromethyl-2H-pyrazol-3-yl)-5,7-dihydro-1H-imidazo[4,5-f]indol-6-one;
5,7,7-Trimethyl-2-(5-trifluoromethyl-2H-pyrazol-3-yl)-5,7-dihydro-3H-imidazo[4,5-f]indol-6-one;
5-Ethyl-2-(5-methoxy-1H-pyrazol-3-yl)-7,7-dimethyl-5,7-dihydro-3H-imidazo[4,5-f]indol-6-one and
5-Ethyl-7,7-dimethyl-2-(5-methylsulfanyl-1H-pyrazol-3-yl)-5,7-dihydro-1H-imidazo[4,5-f]indol-6-one.

9. A compound of claim 1 selected from the group consisting of
3-Methyl-6-(5-methyl-1H-pyrazol-3-yl)-3,5-dihydro-1H-benzo[1,2-d;4,5-d']diimidazol-2-one;
3-Isopropyl-6-(5-methyl-1H-pyrazol-3-yl)-3,5-dihydro-1H-benzo[1,2-d;4,5-d']diimidazol-2-one; and
1-[7,7-Dimethyl-2-(5-methyl-2H-pyrazol-3-yl)-6,7-dihydro-3H-imidazo[4,5-f]indol-5-yl]-ethanone.

10. A process for the preparation of the compounds of the formula

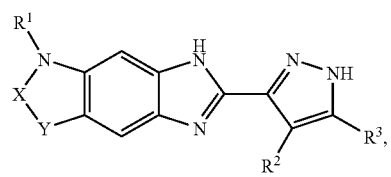

formula I wherein
R¹ is alkyl or —C(O)-alkyl;
R² is hydrogen, alkyl, cyano or halogen;

R³ is hydrogen, alkyl, (C₃-C₆)-cycloalkyl, alkoxy or alkylsulfanyl;
X is —C(O)— or —CH₂—;
Y is —NH—, —CH₂—CR⁴R⁵—, —CR⁴R⁵—CH₂— or —CR⁴R⁵—; wherein
R⁴ is hydrogen or alkyl; and
R⁵ is hydrogen or alkyl,
or alternatively
R⁴ and R⁵ form together with the carbon atom to which they are attached a cycloalkyl ring;
which comprises
a) reacting a compound of formula II

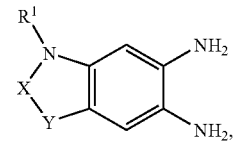

formula II wherein R¹ is alkyl or —C(O)-alkyl and X and Y have the significance given above for formula I;
with a compound of formula III,

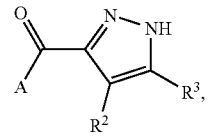

formula III wherein A is —OH, —Cl, —H or —OMe and R² and R³ have the significance given above for formula I;
to give the compounds of formula I,

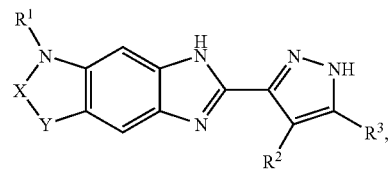

formula I wherein R¹ is alkyl or —C(O)-alkyl and R², R³, X and Y have the significance given above for formula I;
b) isolating said compound of formula I from the reaction mixture, and if desired, converting it into a pharmaceutically acceptable salt.

11. A pharmaceutical composition comprising a compound of formula I

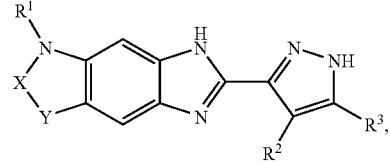

formula I wherein
$R^1$ is alkyl or —C(O)-alkyl;
$R^2$ is hydrogen, alkyl, cyano or halogen;
$R^3$ is hydrogen, alkyl, ($C_3$-$C_6$)-cycloalkyl, alkoxy or alkyl-sulfanyl;
X is —C(O)— or —$CH_2$—;
Y is —NH—, —$CH_2$—$CR^4R^5$—, —$CR^4R^5$—$CH_2$— or —$CR^4R^5$—; wherein
$R^4$ is hydrogen or alkyl; and
$R^5$ is hydrogen or alkyl,
or alternatively
$R^4$ and $R^5$ form together with the carbon atom to which they are attached a cycloalkyl ring;
and all pharmaceutically acceptable salts thereof together with a pharmaceutically acceptable excipient.

* * * * *

UNITED STATES PATENT AND TRADEMARK OFFICE
CERTIFICATE OF CORRECTION

PATENT NO.       : 7,285,569 B2                                Page 1 of 1
APPLICATION NO.  : 11/233408
DATED            : October 23, 2007
INVENTOR(S)      : Georges et al.

It is certified that error appears in the above-identified patent and that said Letters Patent is hereby corrected as shown below:

On Title Page Item (75):

• The Inventor information reads "Georges Guy, Habach (DE); Bernhard Goller, Penzberg (DE); Hans-Willi Krell, Penzberg (DE); Klaus-Peter Kuenkele, Benediktbeuern (DE); Anja Limberg, Penzberg (DE); Petra Rueger, Penzberg (DE); Matthias Rueth, Penzberg (DE)". The Inventor information should read
-- Guy Georges, Habach (DE); Bernhard Goller, Penzberg (DE); Hans-Willi Krell, Penzberg (DE); Klaus-Peter Kuenkele, Benediktbeuern (DE); Anja Limberg, Penzberg (DE); Petra Rueger, Penzberg (DE); Matthias Rueth, Penzberg (DE) --.

On the Title Page, Item (73)
• The Assignee information reads "Hoff Hoffmann-La Roche Inc., Nutley, NJ (US)".
The Assignee information should read -- Hoffmann-La Roche Inc., Nutley, NJ (US) --.

Signed and Sealed this

Twenty-ninth Day of April, 2008

JON W. DUDAS
*Director of the United States Patent and Trademark Office*